US009078864B2

(12) United States Patent
Gudmundsson et al.

(10) Patent No.: US 9,078,864 B2
(45) Date of Patent: Jul. 14, 2015

(54) AGONISTS FOR ANTIMICROBIAL PEPTIDE SYSTEMS

(75) Inventors: Gudmundur Hrafn Gudmundsson, Reykjavik (IS); Birgitta Agerberth, Stockholm (SE); Eirikur Steingrimsson, Reykjavik (IS); Roger Stromberg, Huddinge (SE); Raqib Rubhana, Dhaka (BD)

(73) Assignee: Akthelia Pharmaceuticals, Reykjavik (IS)

(*) Notice: Subject to any disclaimer, the term of this patent is extended or adjusted under 35 U.S.C. 154(b) by 312 days.

(21) Appl. No.: 12/811,741

(22) PCT Filed: Dec. 11, 2008

(86) PCT No.: PCT/IB2008/003709
§ 371 (c)(1),
(2), (4) Date: Jul. 6, 2010

(87) PCT Pub. No.: WO2009/087474
PCT Pub. Date: Jul. 16, 2009

(65) Prior Publication Data

US 2011/0118217 A1 May 19, 2011

Related U.S. Application Data

(60) Provisional application No. 61/019,652, filed on Jan. 8, 2008.

(51) Int. Cl.
*A61K 31/192* (2006.01)
*A61K 31/19* (2006.01)
(Continued)

(52) U.S. Cl.
CPC ................ *A61K 31/192* (2013.01); *A23L 1/30* (2013.01); *A61K 31/198* (2013.01); *A61K 45/06* (2013.01)

(58) Field of Classification Search
CPC ...... A23L 1/30; A61K 31/192; A61K 31/198; A61K 45/06
USPC .......... 514/167, 348, 547, 551, 557, 563, 570
See application file for complete search history.

(56) References Cited

U.S. PATENT DOCUMENTS

| | | | |
|---|---|---|---|
| 4,137,317 | A | 1/1979 | Paris et al. |
| 5,605,930 | A | 2/1997 | Samid |

(Continued)

FOREIGN PATENT DOCUMENTS

| | | | |
|---|---|---|---|
| DE | 19518262 | A1 | 11/1996 |
| DE | 10 2006 026 464 | A1 | 12/2007 |

(Continued)

OTHER PUBLICATIONS

Blasi et al.(Respiration, 2005, vol. 72, pp. 9-25.*

(Continued)

*Primary Examiner* — Savitha Rao
(74) *Attorney, Agent, or Firm* — Meunier Carlin & Curfman LLC

(57) ABSTRACT

Short chain fatty acids (SCFAs) and glycerol esters of SCFAs not previously used for that purpose are provided for use as a medicament for treating, preventing or counteracting microbial infections in animals, including humans, by stimulating the innate antimicrobial peptide defense system. Preferred compounds include phenyl substituted short chain fatty acids (SCFAs) derivatives and. Also provided are methods and compositions for treating, preventing or counteracting microbial infections, including bacterial, viral, fungal, and parasitic infections, by administration of medicaments comprising a secretagogue-effective amount of the compounds of the invention.

12 Claims, 9 Drawing Sheets

Figure 1:
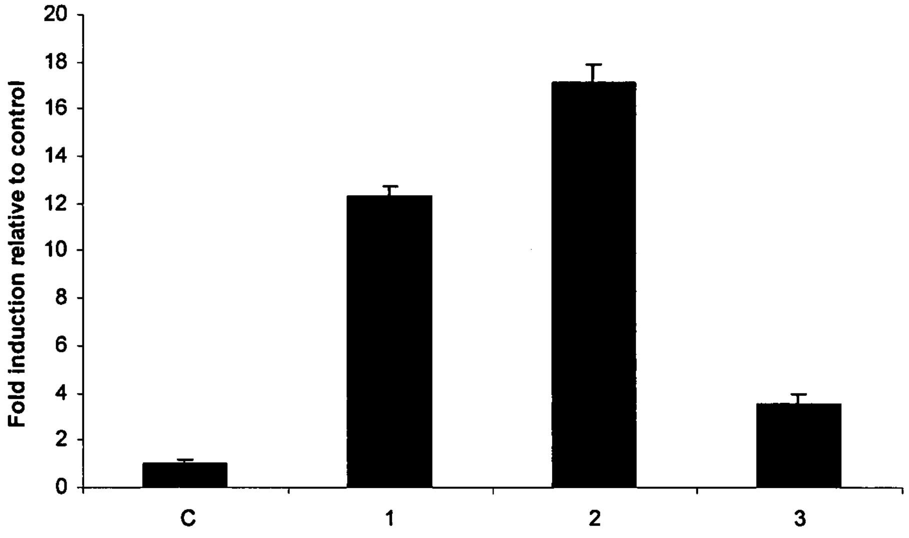

(51) Int. Cl.

*A23L 1/30* (2006.01)
*A61K 31/198* (2006.01)
*A61K 45/06* (2006.01)

(56) References Cited

U.S. PATENT DOCUMENTS

| | | | | |
|---|---|---|---|---|
| 5,618,840 | A | 4/1997 | Wright | |
| 5,635,533 | A | 6/1997 | Samid | |
| 5,852,056 | A | 12/1998 | Samid | |
| 5,883,124 | A | 3/1999 | Samid | |
| 5,939,456 | A | 8/1999 | Perrine | |
| 6,011,000 | A | 1/2000 | Perrine et al. | |
| 6,197,743 | B1 | 3/2001 | Faller | |
| 6,511,800 | B1 | 1/2003 | Singh | |
| 7,049,058 | B2 | 5/2006 | Singh | |
| 7,311,925 | B2 | 12/2007 | Zasloff et al. | |
| 7,396,659 | B2 | 7/2008 | Singh | |
| 7,632,853 | B2 | 12/2009 | Pacheco et al. | |
| 2001/0009922 | A1 | 7/2001 | Faller | |
| 2002/0076393 | A1 | 6/2002 | Fehlbaum et al. | |
| 2002/0115716 | A1 | 8/2002 | Chaturvedi et al. | |
| 2003/0109582 | A1 | 6/2003 | Zasloff | |
| 2003/0113388 | A1 | 6/2003 | Phan | |
| 2003/0133930 | A1 | 7/2003 | Goldenberg et al. | |
| 2003/0206946 | A1 | 11/2003 | Chung | |
| 2004/0043030 | A1 | 3/2004 | Griffiths et al. | |
| 2004/0091506 | A1 | 5/2004 | Bommarito | |
| 2004/0110667 | A1 | 6/2004 | Linn | |
| 2004/0116523 | A1 | 6/2004 | Popoff | |
| 2004/0132817 | A1 | 7/2004 | Finzer et al. | |
| 2004/0152653 | A1 | 8/2004 | Ziady et al. | |
| 2004/0219156 | A1 | 11/2004 | Goldenberg et al. | |
| 2004/0219203 | A1 | 11/2004 | Griffiths et al. | |
| 2004/0241158 | A1 | 12/2004 | McBride et al. | |
| 2005/0037992 | A1 | 2/2005 | Lyons et al. | |
| 2005/0063903 | A1 | 3/2005 | Zeligs | |
| 2005/0079184 | A1 | 4/2005 | Hsing-Chang et al. | |
| 2005/0245439 | A1 | 11/2005 | Chung | |
| 2005/0261342 | A1 | 11/2005 | Kamel et al. | |
| 2005/0272644 | A1 | 12/2005 | Chung | |
| 2006/0018921 | A1 | 1/2006 | Levenson et al. | |
| 2006/0045912 | A1 | 3/2006 | Truog | |
| 2006/0228300 | A1 | 10/2006 | Chang et al. | |
| 2006/0228407 | A1 | 10/2006 | Ziady et al. | |
| 2006/0229237 | A1* | 10/2006 | Chung et al. | 514/9 |
| 2006/0264497 | A1 | 11/2006 | Zeligs | |
| 2006/0275370 | A1 | 12/2006 | Chung et al. | |
| 2006/0276438 | A1 | 12/2006 | Sethuraman et al. | |
| 2007/0021508 | A1 | 1/2007 | Yen et al. | |
| 2007/0072793 | A1 | 3/2007 | Chung | |
| 2007/0086942 | A1 | 4/2007 | Chang et al. | |
| 2007/0141074 | A1 | 6/2007 | Schubert | |
| 2007/0185069 | A1 | 8/2007 | Plum et al. | |
| 2007/0254835 | A1 | 11/2007 | Lyons et al. | |
| 2008/0038374 | A1 | 2/2008 | Stahle et al. | |
| 2008/0107646 | A1 | 5/2008 | Chung et al. | |
| 2008/0166342 | A1 | 7/2008 | Hansen et al. | |
| 2008/0254017 | A1 | 10/2008 | Kane et al. | |
| 2008/0300205 | A1 | 12/2008 | Tsai et al. | |

FOREIGN PATENT DOCUMENTS

| | | | |
|---|---|---|---|
| EP | 1166782 | A2 | 1/2002 |
| EP | 0725635 | B1 | 12/2004 |
| EP | 1523982 | A2 | 4/2005 |
| EP | 1537859 | A2 | 6/2005 |
| EP | 1543839 | A2 | 6/2005 |
| EP | 1249246 | B1 | 9/2005 |
| EP | 1611885 | A1 | 1/2006 |
| EP | 1719508 | A1 | 11/2006 |
| EP | 1719543 | A1 | 11/2006 |
| EP | 1886677 | A1 | 2/2008 |
| EP | 1574213 | B1 | 7/2008 |
| EP | 2030616 | A1 | 3/2009 |
| EP | 2033635 | A1 | 3/2009 |
| JP | 2003 252798 | A | 9/2003 |
| JP | 2005 179290 | A | 7/2005 |
| WO | 98/04290 | A | 2/1998 |
| WO | 98/19545 | A | 5/1998 |
| WO | 98/40078 | A | 9/1998 |
| WO | 00/09137 | A2 | 2/2000 |
| WO | 00/56153 | A1 | 9/2000 |
| WO | 01/08708 | A2 | 2/2001 |
| WO | 02/38181 | A | 5/2002 |
| WO | 03/011342 | A1 | 2/2003 |
| WO | 2004/058298 | | 7/2004 |
| WO | 2004/071425 | A2 | 8/2004 |
| WO | 2004/074434 | A2 | 9/2004 |
| WO | 2004/091307 | A | 10/2004 |
| WO | 2004/091569 | A | 10/2004 |
| WO | 2005/009349 | A2 | 2/2005 |
| WO | 2005/014618 | A1 | 2/2005 |
| WO | 2005/063281 | A2 | 7/2005 |
| WO | 2005/113503 | A2 | 12/2005 |
| WO | 2006/059237 | A1 | 6/2006 |
| WO | 2006/105196 | A2 | 10/2006 |
| WO | 2006/107786 | A2 | 10/2006 |
| WO | 2007/123790 | A | 11/2007 |
| WO | 2008/039472 | A | 4/2008 |
| WO | 2008/073174 | A2 | 6/2008 |

OTHER PUBLICATIONS

E-coli fact sheet (Dec. 2006, retrieved from the internet on Dec. 7, 2011, URL: http://www.health.ny.gov/diseases/communicable/e__coli/docs/fact__sheet.pdf.*

Gombart et al. (The FASEB journal, research communication, 2005, vol. 19 (1067-1077.*

The enteric bacteria, 2004, Downloaded from the internet on Aug. 2, 2012, URL: http://deadlydeceit.com/enteric__bacteria.html.*

Salomao et al., "Chemical Composition and Microbicidal Activity of Extracts from Brazilian and Bulgarian Propolis", Letters in Applied Microbiology 2004 GB, vol. 38, No. 2, 2004, pp. 87-92.

Abd El-Hady, Effect of Egyptian Propolis on the Susceptibility of LDL to Oxidative Modification and its Antiviral Activity with Special Emphasis on Chemical Compostion, Zeitschrift Fuer Naturforschung Section C, Journal of Biosciences, vol. 62, Nos. 9-10, Sep. 2007, pp. 645-655.

Narayana et al., "Biological Act'iv'ity of Phenylpropionic Acid lsolated from a Terrestrial Streptomycetes", Polish Journal of Microbiology, vol. 56, No. 3, 2007, pp. 191-197.

Bankova et al., Chemical Composition and Antibacterial Activity of Brazilian Propolis, Zeitschrift Fuer Naturforschung Section C Biosciences, vol. 50, Nos. 3-4, 1995, pp. 167-172.

Feasley et al., "Effect of Ortho Substituents on the Bacteriostatic Properties of Phenylacetic Acid", Journal of the American Pharmaceutical Association, (1912-1977) (1941), vol. 30, pp. 41-44.

Dong et al., "Antifungal Activity of Crude Extracts and Fat-Soluble Constituents of Holotrichia Diomphalia Larvae", Bioresource Technology, vol. 99, No. 17. Nov. 1, 2008, pp. 8521-8523.

Rabbani, et al., "Short-Chain Fatty Acids Improve Clinical, Pathologic, and Microbiologic Features of Experimental Shigellosis", Journal of Infectious Diseases, vol. 179, No. 2, Feb. 1999, pp. 390-397.

Schauber et al., "Expression of the Cathelicidin LL-37 is Modulated by Short Chain Fatty Acids in Colonocytes: Relevance of Signalling Pathways", Gut, British Medical Association, London, UK, vol. 52, No. 5, May 1, 2003, pp. 735-741.

Raqib et al., "Improved Outcome in Shigellosis Associated with Butyrate Induction of an Endogenous Peptide Antibiotic", Proceedings of the National Academy of Sciences of USA, National Academy of Science, Washington, D.C., U.S., vol. 103, No. 24, Jun. 13, 2006, pp. 9178-9183.

Hase et al., "Cell Differentiation is a Key Determinant of Cathelicidin LL-37 / Human Cationic Antimicrobial Protein 18 Expressin by Human Colon Epithelium", Infection and Immunity, Feb. 2002, vol. 70, No. 2, pp. 953-963.

Hata, et al., "Adminstration of Oral Vitamin D Induces Cathelicidin Production in Atopic Individuals", J Allery Clin. Immunol, Oct. 2008, vol. 122, No. 4.

(56) References Cited

OTHER PUBLICATIONS

Batshaw et al., "Alternative Pathway Therapy for Urea Cycle Disorders: Twenty Years Later", J Pediatr., 2001, vol. 138, No. 1, pp. S46-S55.
Roque et al., "Proinflammatory Effect of Sodium 4-Phenylbutyrale in F508-Cystic Fibrosis Transmembrane Conductance Regulator Lung Epithelial Cells: Involvement of Extracellular Signal-Regulator Protein Kinase 1/2 and c-Jun-NH2-Terminal Kinase Signaling", J Phamiacol Exp. Ther, Sep. 2008, vol. 326(3), pp. 949-956.
Steinmann, J., "Induction of Antimicrobial Peptide Gene Expression in a Bronchial Epithelial Cell Line", Poster for conference, Mar. 15, 2008.
Steinmann, J., "Induction of Antimicrobail Peptide Gene Expression by an Approved Drug in Bronchial Epithelial Cell Line", Abstract for conference, Mar. 15, 2008.
International Search Report, PCT Application No. PCT/IB2008/003709. mailed Jul. 6, 2009.
Sarker, P. et al., Phenylbutyrate Counteracts Shigella Mediated Downregulation of Cathelicidin in Rabbit Lung and Intestinal Epithelia; A Potential Therapeutic Strategy, PLoS ONE, Jun. 3, 2011, 6(6):e20637, 1-10.
Steinmann, J. et al., Phenylbutyrate Induces Antimicrobial Peptide Expression, Anitmicrobial Agents and Chemotherapy, Dec. 2009, 53(12):5127-5133.

* cited by examiner

A

Butyrate (BA)

2,2-dimethylbutyrate (ST20)

4-phenylbutyrate (PBA)

α-methylhydrocinnamate (ST7)

B

A

B

AGONISTS FOR ANTIMICROBIAL PEPTIDE SYSTEMS

CROSS REFERENCE TO RELATED APPLICATIONS

This application is the U.S. National Phase of PCT/IB2008/003709 filed on Dec. 11, 2008 which claims the benefit U.S. Application No. 61/019,652 filed on Jan. 8, 2008, both of which are incorporated herein by reference.

TECHNICAL FIELD

The invention relates to compounds which are active as drugs for stimulating the innate antimicrobial peptide system and can be used as antimicrobial drugs.

BACKGROUND ART

Antimicrobial peptides and proteins play an important role in innate host defenses and are believed to be particularly important at mucosal surfaces that form the initial barrier between the host and the external environment. Such peptides are found in large quantities in the colonic epithelium. The peptides can be considered as endogenous antibiotics and are widespread in nature as immediate defense effectors. They are mainly stored in vacuoles of granulocytes ready for activation upon stimulation or secreted directly onto mucosal and other surfaces by epithelial cells.

A human antimicrobial peptide has been identified and is referred to as LL-37, a 37-residue peptide present in neutrophils, epithelial cells and lymphocytes. Both isolated and chemically synthesised LL-37 show antimicrobial activity in vitro.

Certain bacteria have evolved mechanisms to overcome the antimicrobial peptide barrier, such as *Shigella* bacteria which down-regulate LL-37 expression in the colon epithelium.

Rabbani et al. (*Short-Chain Fatty Acids Improve Clinical, Pathologic, and Microbiologic Features of Experimental Shigellosis. The Journal of Infectious Diseases* 1999; 179: 390-7) investigated that naturally occurring short chain fatty acids (SCFAs; acetate, propionate, and butyrate in 60:30:40 ratio) which occur as fermentation products in the gut. The authors used a rabbit model of shigellosis. They reported that the mixture, given by colonic infusion into the rabbits with acute shigellosis, improved clinical, pathologic, and bacteriologic characteristics.

Hase et al. (*Cell Differentiation Is a Key Determinant of Cathelicidin LL-*37*/Human Cationic Antimicrobial Protein* 18 *Expression by Human Colon Epithelium. INFECTION AND IMMUNITY*, February 2002, vol 70, No 2 p. 953-963) reported that infection in vitro of HCA-7 cells with *Salmonella enterica* serovar Dublin or enteroinvasive *Escherichia coli* modestly upregulated LL-37/hCAP18 mRNA expression. The authors concluded that differentiated human colon epithelium expresses LL-37/hCAP18 as part of its repertoire of innate defense molecules.

Schauber et al. (*Expression of the cathelicidin LL-*37 *is modulated by short chain fatty acids in colonocytes: relevance of signalling pathways*. Gut 2003; 52:735-741.) investigated the effect of naturally occurring SCFAs on LL-37 expression in vivo and in vitro. These authors report that following exposure to butyrate, isobutyrate and propionate, expression of the LL-37 mRNA increases in vitro in colonocytes. The authors are cautious about the possible consequences of increased antimicrobial peptide expression on the commensal intestinal flora, which is critical for protection of the mucosa against enteropathogenic microbes. They note a pathological increase in the activity of endogenous antibiotics would not then be beneficial to the host but might have deleterious consequences.

Raqib et al. (*Improved outcome in shigellosis associated with butyrate induction of an endogenous peptide antibiotic*. Proc. Natl. Acad. Sci. 2006; 103: 9178-9183.) reported that butyrate treatment of rabbits resulted in reduced clinical illness and bacterial load in the stool and significant upregulation of CAP-18 (the rabbit homologue of LL-37) in the surface epithelium.

Other molecules have also been investigated for their possible utility in stimulating natural defensins.

Figure 7:
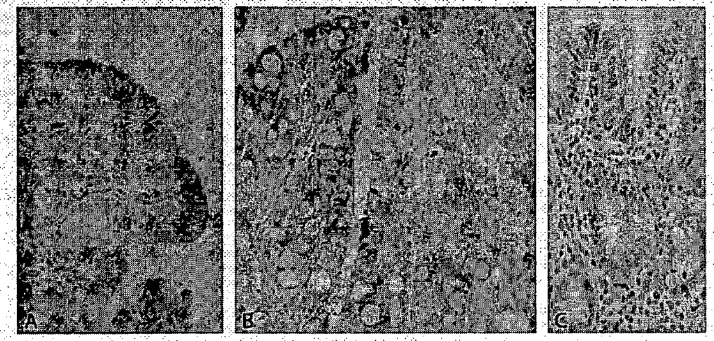

WO2000-09137 (Magainin Pharmaceuticals) describes newly isolated aminosterol compounds and pharmaceutical compositions based on the aminosterol compounds are described. Methods for the treatment of various disorders, for example, a microbial infection, are also described US2002-0076393 (Fehlbaum et al.) describe the use of isoleucine or active isomers or analogs thereof for stimulating production of defensin. It should be noted that the claims refer, inter alia, to one such analog being butyrate or an active derivative thereof. However where butyrate was tested and it appeared to be less active than isoleucine at similar concentrations (see FIG. 7 therein).

US2003-0109582 (Zasloff) describe the use of isoleucine compounds for stimulating Paneth cells to release natural antimicrobial agents including peptides, to reduce or eliminate pathogenic organisms in the GI tract of mammalian bodies, including humans, utilizing an active isoleucine compound as a secretagogue. "Isoleucine compounds" are defined as including 'isoleucine butyrate' though this compound is not described or tested.

U.S. Pat. No. 7,311,925 (Zasloff) describes methods of blocking microbial adherence to a eukaryotic cell surface in a mammal by applying a pharmacologically acceptable composition containing at least one compound selected from the group consisting of isoleucine, an active isomer thereof, and an active analog thereof, to said surface in a microbial blocking quantity. Active analogs of isoleucine are defined as including 'isoleucine butyrate' though this compound is not described or tested.

US20080038374 (Stahle) describes use of a vitamin D compound, which is able to specifically and directly upregulate hCAP18, for the manufacturing of a medicament with antimicrobial effect for treatment of conditions deficient in LL-37, such as chronical ulcers, and atopic dermatitis.

WO/2008/073174 (GALLO) describes methods and compositions for modulating gene expression and cathelicidin the innate immune response by 1,25$(OH)_2$ vitamin D3 (1,25D3). That compound is tested alongside non-specific histone deacetylase inhibitors (HDACi) including butyrate or trichostatin A.

Hata et al. (2008) "*Administration of oral vitamin D induces cathelicidin production in atopic individuals*" J ALLERGY CLIN IMMUNOL, VOLUME 122, NUMBER 4, described a study in which 14 normal controls and 14 atopic subjects with moderate to severe atopic dermatitis were treated with oral vitamin D3 to see if this could overcome the relative deficiency in induction of cathelicidin in the atopic patients. After supplementation with 4000 IU/d oral vitamin D for 21 days, AD lesional skin showed a statistically significant increase in cathelicidin expression.

Despite the above disclosures, it will be appreciated that the provision of compounds or combinations of compounds for use in enhancing the innate immune response, for example in the gut, would provide a contribution to the art.

SUMMARY OF THE INVENTION

As can be seen from the discussion above, the publications in the art had been cautious about the possible deleterious consequences of SCFA compounds which stimulate the effect of endogenous antibiotics in the human gut, because of their potential effect on commensal intestinal flora. Additionally, it was known that butyrate, for example, had practical drawbacks, in particular the unpleasant odour and taste, that made it unsuitable for pharmaceutical use. These reasons may account for the fact that the effect of SCFAs had not been investigated in the art in humans but greater interest has apparently been given to the use of vitamin D in the skin.

The present inventors have found that a number of pharmaceutically acceptable SCFA-derivatives and prodrugs are active as drugs to stimulate the innate antimicrobial peptide system in human cell lines and can be used as preventive and curative antimicrobial drugs in animal models of disease. These pharmaceutically acceptable SCFA-derivatives may be more acceptable (in terms of odour and\or taste) than butyrate. These findings have profound implications for the use of these compounds on replacing or supplementing existing antibiotics or other antimicrobial strategies in treating human disease.

An abstract has previously been made available stating that an unidentified drug stimulated cathelicidin antimicrobial peptide (CAMP) and human beta-defensin 1 (hBD-1) gene expression in the bronchial epithelial cell line VA10 ("Induction of Antimicrobial Peptide Gene Expression by a approved drug in a Bronchial Epithelial Cell Line"; Jónas Steinmann and Guð mundur Hrafn Guð mundsson, Institute of Biology, University of Iceland, Sturlugata 7, 101 Reykjavik, Iceland).

After the presently claimed priority date, a poster was presented showing for the first time that 4-phenylbutyrate (PBA) stimulates cathelicidin antimicrobial peptide gene expression in a bronchial epithelial cell line ("Induction of Antimicrobial Peptide Gene Expression in a Bronchial Epithelial Cell Line"; Jonas Steinmann and Guð mundur Hrafn Guð mundsson Institute of Biology, University of Iceland, 101 Reykjavik, Iceland; 15 Mar. 2008).

Sodium phenylbutyrate is a known medicament. For example it has been marketed by Ucyclyd Pharma (Hunt Valley, USA) under the trade name Buphenyl and by Swedish Orphan International (Sweden) as Ammonaps. It has been used to treat urea cycle disorders (Batshaw et al. (2001) *J. Pediatr.* 138 (1 Suppl): S46-54; discussion S54-5). Scandinavian Formulas, Inc. Sellersville, Pa. supplies sodium phenylbutyrate worldwide for clinical trials. Sodium phenylbutyrate is also under investigation for the treatment of some sickle-cell disorders (Blood Products Plasma Expanders and Haemostatics) and for use as a potential differentiation-inducing agent in malignant glioma and acute myeloid leukaemia. It has also been investigated in respect of cystic fibrosis pathology due to its capacity to traffic DeltaF508-cystic fibrosis transmembrane conductance regulator (CFTR) to the cell membrane and restore CFTR chloride function at the plasma membrane of CF lung cells in vitro and in vivo (Roque et al. J Pharmacol Exp Ther. 2008 September; 326(3):949-56. Epub 2008 Jun. 23). It is believed in the literature that phenylbutyrate is a prodrug which is metabolized in the body by beta-oxidation to phenylacetate.

Notwithstanding the above, prior to the present invention, PBA was not known or suggested for the uses claimed herein.

DETAILED DISCLOSURE OF THE INVENTION

Thus in a first aspect, the present invention provides compounds as defined by formula I for use as a medicament for treating, preventing or counteracting microbial infections in humans and animals by stimulating the innate antimicrobial peptide defense system, Compounds of the Invention In a first aspect, the present invention provides compounds as defined by formula Ia for use as a medicament for treating, preventing or counteracting microbial infections in humans and animals by stimulating the innate antimicrobial peptide defense system, (Ia)

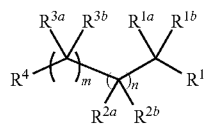

wherein $R^1$ represents a carboxyl group, phosphate, phosphonate or sulfonate group or pharmaceutically acceptable salt thereof, $COOR^5$, $CONH_2$, $CONR^5R^6$, or an aldehyde, imine or acetal protected derivative of said compounds, or a triglyceride moiety $COOCH_2CH(OOCR^5)CH_2(OOCR^6)$ or diglyceride moiety $COOCH_2CH(OOCR^5)CH_2OH$, or an amino acid group $CONHCR^7COOH$ or a salt thereof;

m and n are each independently 0 or 1;

$R^{1a}$, $R^{1b}$, $R^{2a}$, $R^{2b}$, $R^{3a}$ and $R^{3b}$ each independently represent hydrogen, halide, amino, hydroxyl, carbonyl, a linear or branched substituted or nonsubstituted saturated or nonsaturated alkyl group with 1 to 10 carbon atoms, or a substituted or nonsubstituted aryl group; and/or $R^{2a}$, together with an adjacent $R^{3a}$ or $R^{1a}$, may represent a carbon-carbon $\pi$ bond; and/or $R^{2b}$, together with an adjacent $R^{3b}$ or $R^{1b}$, may represent a carbon-carbon $\pi$ bond;

$R^4$ may be hydrogen, halide, amino, hydroxyl, carbonyl, a linear or branched substituted or nonsubstituted saturated or nonsaturated alkyl group with 1 to 10 carbon atoms, or a substituted or nonsubstituted aryl group;

$R^5$ represents a linear or branched substituted or nonsubstituted saturated or nonsaturated alkyl group with 1 to 10 carbon atoms or a substituted or nonsubstituted aryl group;

$R^6$ represents hydrogen, a linear or branched substituted or nonsubstituted saturated or nonsaturated alkyl group with 1 to 10 carbon atoms or a substituted or nonsubstituted aryl group; and $R^7$ is a side chain of a naturally occurring amino acid or is selected from $CH_2CH_2CH_2NHR^8$, $CH_2CH_2CH_2CH_2NHR^8$, or $CH_2CH_2CH_2NHC({=}NH)NHR^8$, where $R^8$ is hydrogen or a linear or branched acyl group with three to five carbon atoms;

and wherein, if $R^1$ is carboxyl or a salt thereof, at least one of $R^{1a}$, $R^{1b}$, $R^{2a}$, $R^{2b}$, $R^{3a}$, $R^{3b}$ and $R^4$ is selected from halide, amino, hydroxyl, carbonyl, a linear or branched substituted or nonsubstituted saturated or nonsaturated alkyl group with 1 to 10 carbon atoms, or a substituted or nonsubstituted aryl group.

In some embodiments the compound may be a compound of formula I:

(I)

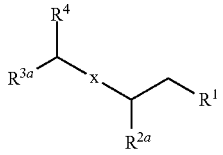

wherein, preferably, $R^1$ represents a carboxyl group, phosphate, phosphonate or sulfonate group or pharmaceutically acceptable salt thereof, $COOR^5$, $CONH_2$, $CONR^5R^6$, or an aldehyde, imine or acetal protected derivative of said compounds, or a triglyceride moiety $COOCH_2CH(OOCR^5)CH_2(OOCR^6)$ or diglyceride moiety $COOCH_2CH(OOCR^5)CH_2OH$, or an amino acid group $CONHCR^7COOH$ or a salt thereof, $R^{2a}$ represents hydrogen, hydroxyl, carbonyl, or a linear or branched substituted or nonsubstituted saturated or nonsaturated alkyl group with 1 to 10 carbon atoms or substituted or nonsubstituted aryl group, $R^{3a}$ represents hydrogen, hydroxyl, carbonyl, or a linear or branched substituted or nonsubstituted saturated or nonsaturated alkyl group with 1 to 10 carbon atoms or substituted or nonsubstituted aryl group, except when $R^1$ is carboxyl or a salt thereof. $R^{3a}$ is not hydrogen, $R^4$ represents hydrogen, or a linear or branched substituted or nonsubstituted saturated or nonsaturated alkyl group with 1 to 10 carbon atoms or substituted or nonsubstituted aryl group, x represents a single, double or triple bond, or x-$R^{3a}R^4$ together represent hydrogen in which case $R^1$ is preferably $COOR^5$, $CONH_2$, $CONR^5R^6$, or a triglyceride moiety $COOCH_2CH(OOCR^5)CH_2(OOCR^6)$ or diglyceride moiety $COOCH_2CH(OOCR^5)CH_2OH$, $R^5$ represents a linear or branched substituted or nonsubstituted saturated or nonsaturated alkyl group with 1 to 10 carbon atoms or substituted or nonsubstituted aryl group, $R^6$ represents hydrogen, a linear or branched substituted or nonsubstituted saturated or nonsaturated alkyl group with 1 to 10 carbon atoms or substituted or nonsubstituted aryl group, and $R^7$ represents $CH_2CH_2SCH_3$, $CH_2CH_2CH_2NHR^8$, $CH_2CH_2CH_2CH_2NHR^8$, $CH_2CH_2CH_2NHC(=NH)NHR^8$, where $R^8$ is hydrogen or a linear or branched acyl group with three to five carbon atoms.

Compounds of formula I are compounds of formula Ia in which $R^{1a}$ and $R^{1b}$ are both hydrogen, m and n are both 1, and $R^{2b}$ and $R^{3b}$ are either both hydrogen or together form a π bond in position 'x'. If $R^{2a}$ and $R^{3a}$ also together form a it bond, then position 'x' represents a double bond.

Compounds of formula Ia in which $R^{1a}$, $R^{1b}$ and $R^{2b}$ are all hydrogen, m is 0, n is 1, and $R^4$ is hydrogen can also be represented as compounds of formula I where x-$R^{3a}R^4$ together represent hydrogen.

In compounds of formula I, 'x' is preferably a single bond.

Preferences for $R^1$

In certain preferred embodiments, the compound of the invention is a carboxylic acid, in these cases $R^1$ represents a carboxyl group, or a pharmaceutically acceptable salt thereof. If $R^1$ is carboxyl or a salt thereof, at least one of $R^{1a}$, $R^{1b}$, $R^{2a}$, $R^{2b}$, $R^{3a}$, $R^{3b}$ and $R^4$ is a substituent other than hydrogen. In other preferred embodiments, $R^1$ is a carboxylic acid derivative, such as an ester or an amide.

In some such embodiments, as represented by formula IIa, $R^1$ is an ester group of formula $COOR^5$ where $R^5$ represents a linear or branched substituted or nonsubstituted saturated or nonsaturated alkyl group with 1 to 10 carbon atoms, and preferably 3 to 5 carbon atoms, or a substituted or nonsubstituted aryl group such as for example phenyl, or benzyl. Particularly preferred $R^5$ groups are methyl and ethyl.

(IIa)

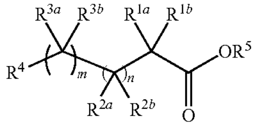

In some preferred embodiments $R^1$ is an ester selected from a triglyceride ester moiety or diglyceride ester moiety.

If $R^1$ is a triglyceride moiety the compounds of the invention are of the following general formula (IIb):

(IIb)

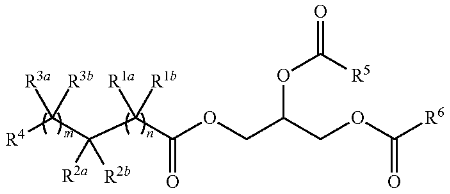

If $R^1$ is a diglyceride moiety, the compounds of the invention are of the following general formula (IIc):

(IIc)

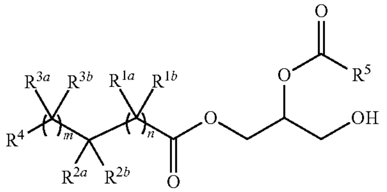

Embodiments of particular interest include glyceryl tributyrate or glyceryl tripropionate. Other preferred embodiments make use of corresponding glycerol esters of one or more phenyl substituted fatty acids or other short chain fatty acids such as the above mentioned. Such glyceryl triesters include for example but not limited to glyceryl tributyrate wherein one or more of the butyrate acyl chains are substituted with phenyl, e.g. 1-butanoyloxy-3-(4'-phenylbutanoyloxy)propan-2-ylbutanoate, 1,3-(4',4"-diphenyl)-di(butanoyloxy)propan-2-yl butanoate, and 1,3-di(butanoyloxy)propan-2-yl-4-phenylbutanoate.

Further embodiments which are carboxylic derivatives embodiments include amides of formula (IId), wherein $R^1$ is a group of formula $CONR^5R^6$, wherein $R^5$ represents a linear or branched substituted or nonsubstituted saturated or nonsaturated alkyl group with 1 to 10 carbon atoms, preferably 3 to 5 carbon atoms, or a substituted or nonsubstituted aryl group such as for example phenyl, or benzyl, and $R^6$ is selected from hydrogen, a linear or branched substituted or nonsubstituted saturated or nonsaturated alkyl group with 1 to 10 carbon atoms, preferably 3 to 5 carbon atoms, or a substituted or nonsubstituted aryl group such as for example phenyl, or benzyl.

(IId)

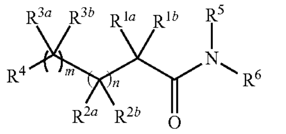

In certain embodiments $R^1$ is an amino acid group, in which case the compounds of the invention may be represented as compounds of the following general formula (IIe):

(IIe)

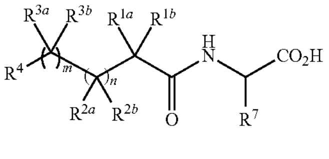

or a salt thereof, in which $R^7$ is an amino acid side chain. In some embodiments $R^7$ is the side chain of a naturally occurring amino acid.

For example, $R^7$ may be a side chain of leucine ($CH_2CH_2CH_2CH_3$), isoleucine ($CH(CH_3)CH_2CH_3$), methionine ($—CH_2CH_2SCH_3$), lysine ($—CH_2CH_2CH_2CH_2NH_2$), or arginine ($—CH_2CH_2CH_2NHC(=NH)NH_2$). In some embodiments, particularly if $R^{1a}$, $R^{1b}$, $R^{2a}$, $R^{2b}$, $R^{3a}$, $R^{3b}$ and $R^4$ are all hydrogen and m and n are 1, $R^7$ is preferably not an isoleucine side chain ($CH(CH_3)CH_2CH_3$).

Alternatively, $R^7$ may be a derivative or analogue of a naturally occurring amino acid side chain, such as a lysine side chain derivative ($—CH_2CH_2CH_2CH_2NHR^8$), an arginine side chain derivative ($—CH_2CH_2CH_2NHC(=NH)NHR^8$), or a group such as $—CH_2CH_2CH_2NHR^8$, wherein $R^8$ represents hydrogen, a linear or branched substituted or unsubstituted saturated or nonsaturated alkyl group with 1 to 10 carbon atoms or substituted or nonsubstituted aryl group.

In certain embodiments found to be useful, the compounds of the invention are relatively small SCFA derivatives. For example, compounds of formula I wherein $R^{2a}$ and $R^4$ represent hydrogen. In these embodiments $R^{3a}$ is preferably hydrogen, hydroxyl, or a substituted or nonsubstituted aryl group including phenyl, or benzyl, with the above limitation applying to $R^{3a}$ in the case where $R^1$ is carboxyl or a salt thereof. Substituted aryl can be hydroxyl or amino-substituted phenyl, or benzyl.

Preferred Chain Lengths

In some preferred compounds of the invention, m and n are each 1. These compounds may be described as butyric acid/butyrate derivatives and are of general formula (IIIa):

(IIIa)

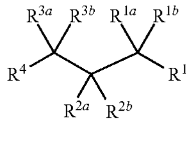

where $R^1$, $R^{1a}$, $R^{1b}$, $R^{2a}$, $R^{2b}$, $R^{3a}$, $R^{3b}$ and $R^4$ are as previously defined.

In other preferred compounds, m is 1 and n is 0. These compounds may be described as propionic acid/propionate derivatives and are of general formula (IIIb):

(IIIb)

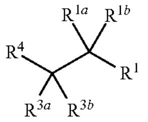

where $R^1$, $R^{1a}$, $R^{1b}$, $R^{2a}$, $R^{2b}$, $R^{3a}$, $R^{3b}$ and $R^4$ are as previously defined. It can be seen that if m were 0 and n were 1, this would also result in propionic acid derivatives.

In some embodiments, both m and n may be 0. This results in compounds which may be described as acetic acid/acetate derivatives, of general formula (IIIc):

(IIIc)

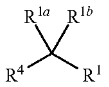

Preferred Substituents

Preferred embodiments of the invention include compounds which are substituted butyric, propionic or acetic acid derivatives of general formulae (IIIa) to (IIIc), wherein $R^1$ is carboxylate or a derivative thereof as defined above and wherein one or more of $R^{1a}$, $R^{1b}$, $R^{2a}$, $R^{2b}$, $R^{3a}$, $R^{3b}$ and $R^4$ is a substituent other than hydrogen, preferably selected from an alkyl group or an aryl group. It is preferred that one or more, preferably one, of $R^{1a}$, $R^{2a}$, $R^{2b}$, $R^{3a}$, $R^{3b}$ and $R^4$ is an aryl group, most preferably a phenyl or substituted phenyl group. When one of $R^{1a}$, $R^{1b}$, $R^{2a}$, $R^{2b}$, $R^{3a}$, $R^{3b}$ and $R^4$ is an aryl group, it is preferred that the others are selected from hydrogen or an alkyl group, the alkyl group being preferably methyl.

Most preferably, $R^4$ is an aryl group, preferably phenyl or substituted phenyl. Certain preferred compounds according to these embodiments are of general formula (IVa):

(IVa)

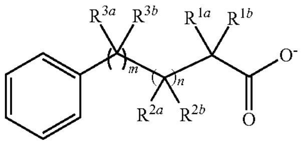

Preferred butyric acid derivatives are therefore of general formula (IVb):

(IVb)

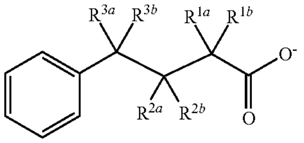

preferred propionic acid derivatives are of general formula (IVC):

(IVc)

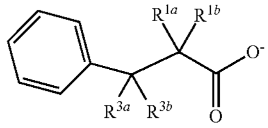

and preferred acetate derivatives are of general formula (IVd):

(IVd)

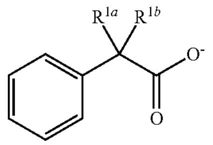

In formulae (IVa) to (IVd), the phenyl ring may optionally be substituted with one or more substituents, as further defined below. Preferred substituents are alkyl, halide, hydroxyl and amino.

The carboxylate group may optionally be derivatised as an ester or amide, as set out above. In these embodiments, $R^{1a}$, $R^{1b}$, $R^{2a}$, $R^{2b}$, $R^{3a}$, $R^{3b}$ are preferably hydrogen or an alkyl group with 1 to 10 carbon atoms, the alkyl group being preferably methyl or ethyl.

In alternative embodiments, $R^4$ may be hydrogen, and one or more, preferably one, of $R^{1a}$, $R^{1b}$, $R^{2a}$, $R^{2b}$, $R^{3a}$, $R^{3b}$ may be an aryl group such as phenyl or substituted phenyl.

Substituents α to the Carboxylate $R^{1a}$ and $R^{1b}$ are preferably selected from hydrogen and an alkyl group having from 1 to 10 carbon atoms, the alkyl group being preferably methyl or ethyl. In some embodiments, $R^{1a}$ and $R^{1b}$ may both be alkyl, but it is preferred that at least one of $R^{1a}$ and $R^{1b}$ is hydrogen.

In particular, the following compounds are useful in accordance with the invention: 4-phenylbutyric acid, 3-phenylbutyric acid, 2-phenylbutyric acid, 3-phenylpropionic acid, 2-phenylpropionic acid, 2-methyl-3-phenylpropionic acid [ST7], 2-methyl-4-phenylbutyric acid, or a pharmaceutically acceptable salt of any of said compounds, methyl 4-phenylbutyrate, ethyl 4-phenylbutyrate, methyl 3-phenylbutyrate, ethyl 3-phenylbutyrate, methyl 2-phenylbutyrate, ethyl 2-phenylbutyrate, methyl 3-phenylpropionate, ethyl 3-phenylpropionate, methyl 2-phenylpropionate, ethyl 2-phenylpropionate, methyl 2-methyl-3-phenylpropionate, ethyl 2-methyl-3-phenylpropionate, methyl 2-methyl-4-phenylbutyrate, and ethyl 2-methyl-4-phenylbutyrate.

Metabolites of these compounds may also be useful in the invention, in particular phenyl acetate.

Substituents β to the Carboxylate (where Present)

In embodiments, one or both of $R^{2a}$ and $R^{2b}$ may optionally be hydroxyl. This may be preferred where it is desired that the compound of the invention have increased resistance to metabolism such as beta oxidation, and hence in principle a longer half-life.

Definitions and Further Preferences

Alkyl:

As used herein the term "alkyl", unless otherwise specified, refers to a $C_{1-10}$ alkyl group, that is to say a monovalent moiety obtained by removing a hydrogen atom from a hydrocarbon compound having from 1 to 10 carbon atoms, which may be aliphatic or alicyclic, or a combination thereof, which may be linear or branched, and which may be saturated, partially unsaturated, or fully unsaturated. In certain instances $C_{1-4}$, $C_{1-5}$, $C_{1-6}$ or $C_{1-7}$ alkyl groups may be preferred.

Examples of saturated linear $C_{1-10}$ alkyl groups include, but are not limited to, methyl, ethyl, n-propyl, n-butyl, n-pentyl (amyl) and n-hexyl.

Examples of saturated branched $C_{1-10}$ alkyl groups include, but are not limited to, iso-propyl, iso-butyl, sec-butyl, tert-butyl, and neo-pentyl.

Examples of saturated alicyclic $C_{1-10}$ alkyl groups (which may also be referred to as "$C_{3-10}$ cycloalkyl" groups) include, but are not limited to, groups such as cyclopropyl, cyclobutyl, cyclopentyl, and cyclohexyl, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

Unsaturated alkyl groups contain one or more double or triple bonds i.e. one or more carbon-carbon π bonds. Examples of unsaturated $C_{1-10}$ alkyl groups which have one or more carbon-carbon double bonds (also referred to as "$C_{2-10}$alkenyl" groups) include, but are not limited to, ethenyl (vinyl, $-CH{=}CH_2$), 2-propenyl (allyl, $-CH-CH{=}CH_2$), isopropenyl ($-C(CH_3){=}CH_2$), butenyl, pentenyl, and hexenyl.

Examples of unsaturated $C_{1-10}$ alkyl groups which have one or more carbon-carbon triple bonds (also referred to as "$C_{2-10}$ alkynyl" groups) include, but are not limited to, ethynyl (ethinyl) and 2-propynyl (propargyl).

Examples of unsaturated alicyclic (carbocyclic) $C_{1-10}$ alkyl groups which have one or more carbon-carbon double bonds (also referred to as "$C_{3-10}$cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

Aryl:

As used herein the term "aryl", unless otherwise specified, refers to a $C_{5-20}$ aryl group, that is to say a monovalent moiety obtained by removing a hydrogen atom from an aromatic ring atom of a $C_{5-20}$ aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups", in which case the group may conveniently be referred to as a "$C_{5-20}$ carboaryl" group.

Examples of $C_{5-20}$ aryl groups which do not have ring heteroatoms (i.e. $C_{5-20}$ carboaryl groups) include, but are not limited to, those derived from benzene (i.e. phenyl) ($C_6$), naphthalene ($C_{10}$), anthracene ($C_{14}$), phenanthrene ($C_{14}$), naphthacene ($C_{18}$), and pyrene ($C_{16}$).

Examples of aryl groups which comprise fused rings, one of which is not an aromatic ring, include, but are not limited to, groups derived from indene and fluorene.

Alternatively, the ring atoms may include one or more heteroatoms, including but not limited to oxygen, nitrogen, and sulphur, as in "heteroaryl groups". In this case, the group may conveniently be referred to as a "$C_{5-20}$ heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of $C_{5-20}$ heteroaryl groups include, but are not limited to, $C_5$ heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, and oxatriazole; and $C_6$ heteroaryl groups derived from isoxazine, pyridine (azine), pyridazine (1,2-diazine), pyrimidine (1,3-diazine; e.g., cytosine, thymine, uracil), pyrazine (1,4-diazine), triazine, tetrazole, and oxadiazole (furazan).

Examples of $C_{5-20}$ heteroaryl groups which comprise fused rings, include, but are not limited to, $C_9$ heterocyclic groups derived from benzofuran, isobenzofuran, indole, isoindole, purine (e.g., adenine, guanine), benzothiophene, benzimidazole; $C_{10}$ heterocyclic groups derived from quinoline, isoquinoline, benzodiazine, pyridopyridine, quinoxaline; $C_{13}$ heterocyclic groups derived from carbazole, dibenzothiophene, dibenzofuran; $C_{14}$ heterocyclic groups derived from acridine, xanthene, phenoxathiin, phenazine, phenoxazine, phenothiazine.

Optional Substitution:

The above alkyl and aryl groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

$C_{1-7}$ alkoxy: —OR, wherein R is a $C_{1-7}$ alkyl group. Examples of $C_{1-7}$ alkoxy groups include, but are not limited to, $—OCH_3$ (methoxy), $—OCH_2CH_3$ (ethoxy) and $—OC(CH_3)_3$ (tert-butoxy).

Oxo (keto, -one): ═O; carbonyl (>C═O). Examples of cyclic compounds and/or groups having, as a substituent, an oxo group (═O) include, but are not limited to, carbocyclics such as cyclopentanone and cyclohexanone; heterocyclics, such as pyrone, pyrrolidone, pyrazolone, pyrazolinone, piperidone, piperidinedione, piperazinedione, and imidazolidone; cyclic anhydrides, including but not limited to maleic anhydride and succinic anhydride; cyclic carbonates, such as propylene carbonate; imides, including but not limited to, succinimide and maleimide; lactones (cyclic esters, —O—C(═O)— in a ring), including, but not limited to, β-propiolactone, γ-butyrolactone, δ-valerolactone, and ϵ-caprolactone; and lactams (cyclic amides, —NH—C(═O)— in a ring), including, but not limited to, β-propiolactam, γ-butyrolactam (2-pyrrolidone), δ-valerolactam, and ϵ-caprolactam.

Imino (imine): ═NR, wherein R is an imino substituent, for example, hydrogen, $C_{1-7}$ alkyl group, a $C_{3-20}$heterocyclyl group, or a $C_{5-20}$ aryl group, preferably hydrogen or a $C_{1-7}$ alkyl group. Examples of ester groups include, but are not limited to, ═NH, ═NMe, ═NEt, and ═NPh.

Formyl (carbaldehyde, carboxaldehyde): —C(═O)H.

Acyl (keto): —C(═O)R, wherein R is an acyl substituent, for example, a $C_{1-7}$alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, $—C(═O)CH_3$ (acetyl), $—C(═O)CH_2CH_3$ (propionyl), $—C(═O)C(CH_3)_3$ (butyryl), and —C(═O)Ph (benzoyl, phenone).

Carboxy (carboxylic acid): —COOH.

Ester (carboxylate, carboxylic acid ester, oxycarbonyl): —C(═O)OR, wherein R is an ester substituent, for example, a $C_{1-7}$ alkyl group, a $C_{3-20}$ heterocyclyl group, or a $C_{5-20}$ aryl group, preferably a $C_{1-7}$alkyl group. Examples of ester groups include, but are not limited to, $—C(═O)OCH_3$, $—C(═O)OCH_2CH_3$, $—C(═O)OC(CH_3)_3$, and —C(═O)OPh.

Acyloxy (reverse ester): —OC(═O)R, wherein R is an acyloxy substituent, for example, a $C_{1-7}$ alkyl group, a $C_{3-20}$ heterocyclyl group, or a $C_{5-20}$ aryl group, preferably a $C_{1-7}$alkyl group. Examples of acyloxy groups include, but are not limited to, $—OC(═O)CH_3$ (acetoxy), $—OC(═O)CH_2CH_3$, $—OC(═O)C(CH_3)_3$, —OC(═O)Ph, and $—OC(═O)CH_2Ph$.

Amido (carbamoyl, carbamyl, aminocarbonyl, carboxamide): $—C(═O)NR^{N1}R^{N2}$, wherein $R^{N1}$ and $R^{N2}$ are independently amino substituents, as defined for amino groups. Examples of amido groups include, but are not limited to, $—C(═O)NH_2$, $—C(═O)NHCH_3$, $—C(═O)N(CH_3)_2$, $—C(═O)NHCH_2CH_3$, and $—C(═O)N(CH_2CH_3)_2$, as well as amido groups in which $R^{N1}$ and $R^{N2}$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): $—NR^{A1}C(═O)R^{A2}$, wherein $R^{A1}$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and $R^{A2}$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, $—NHC(═O)CH_3$, $—NHC(═O)CH_2CH_3$, and —NHC(═O)Ph. $R^{A1}$ and $R^{A2}$ may together form a cyclic structure, as in, for example, succinimidyl, maleimidyl and phthalimidyl:

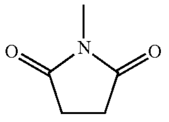
succinimidyl

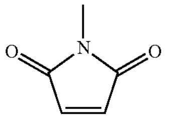
maleimidyl

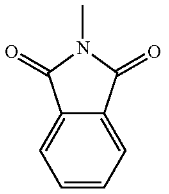
phthalimidyl

Acylureido: $—N(R^{U1})C(O)NR^{U2}C(O)R^{A3}$ wherein $R^{U1}$ and $R^{U2}$ are independently ureido substituents, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. $R^{A3}$ is an acyl group as defined for acyl groups. Examples of acylureido groups include, but are not limited to, —NHCONHC(O)H, —NHCONMeC(O)H, —NHCONEtC(O)H, —NHCONMeC(O)Me, —NHCONEtC(O)Et, —NMeCONHC(O)Et, —NMeCONHC(O)Me, —NMeCONHC(O)Et, —NMeCONMeC(O)Me, —NMeCONEtC(O)Et, and —NMeCONHC(O)Ph.

Carbamate: $—NR^{N1}—C(O)—OR^{O2}$ wherein $R^{N1}$ is an amino substituent as defined for amino groups and $R^{O2}$ is an ester group as defined for ester groups. Examples of carbamate groups include, but are not limited to, —NH—C(O)—O-Me, —NMe-C(O)—O-Me, —NH—C(O)—O-Et, —NMe-C(O)—O-t-butyl, and —NH—C(O)—O-Ph.

Thioamido (thiocarbamyl): $—C(═S)NR^{N1}R^{N2}$ wherein $R^{N1}$ and $R^{N2}$ are independently amino substituents, as defined for amino groups. Examples of amido groups include, but are not limited to, —C(=S)$NH_2$, —C(=S)$NHCH_3$, —C(=S)N$(CH_3)_2$, and —C(=S)$NHCH_2CH_3$.

Tetrazolyl: a five membered aromatic ring having four nitrogen atoms and one carbon atom,

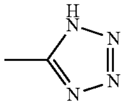

Amino: —$NR^{N1}R^{N2}$, wherein $R^{N1}$ and $R^{N2}$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$alkyl group, or, in the case of a "cyclic" amino group, $R^{N1}$ and $R^{N2}$, taken together with the nitrogen atom to which they are attached, form a heterocyclic ring having from 4 to 8 ring atoms. Examples of amino groups include, but are not limited to, —$NH_2$, —$NHCH_3$, —NHC$(CH_3)_2$, —$N(CH_3)_2$, —$N(CH_2CH_3)_2$, and —NHPh. Examples of cyclic amino groups include, but are not limited to, aziridino, azetidino, pyrrolidino, piperidino, piperazino, morpholino, and thiomorpholino.

Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$ alkyl group.

Amidine: —C(=NR)$NR_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. An example of an amidine group is —C(=NH)$NH_2$.

Carbazoyl (hydrazinocarbonyl): —C(O)—NN—$R^{N1}$ wherein $R^{N1}$ is an amino substituent as defined for amino groups. Examples of azino groups include, but are not limited to, —C(O)—NN—H, —C(O)—NN-Me, —C(O)—NN-Et, —C(O)—NN-Ph, and —C(O)—NN—$CH_2$-Ph.

Nitro: —$NO_2$.

Nitroso: —NO.

Azido: —$N_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —$SCH_3$ and —$SCH_2CH_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —$SSCH_3$ and —$SSCH_2CH_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —S(=O)$_2CH_3$ (methanesulfonyl, mesyl), —S(=O)$_2$$CF_3$ (triflyl), —S(=O)$_2CH_2CH_3$, —S(=O)$_2C_4F_9$ (nonaflyl), —S(=O)$_2CH_2CF_3$ (tresyl), —S(=O)$_2$Ph (phenylsulfonyl), 4-methylphenylsulfonyl (tosyl), 4-bromophenylsulfonyl (brosyl), and 4-nitrophenyl (nosyl).

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)$CH_3$ and —S(=O)$CH_2CH_3$.

Sulfonyloxy: —OS(=O)$_2$R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group.

Examples of sulfonyloxy groups include, but are not limited to, —OS(=O)$_2CH_3$ and —OS(=O)$_2CH_2CH_3$.

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)$CH_3$ and —OS(=O)$CH_2CH_3$.

Sulfamino: —$NR^{N1}$S(=O)$_2$OH, wherein $R^1$ is an amino substituent, as defined for amino groups. Examples of sulfamino groups include, but are not limited to, —NHS(=O)$_2$OH and —N($CH_3$)S(=O)$_2$OH.

Sulfinamino: —$NR^{N1}$S(=O)R, wherein $R^{N1}$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)$CH_3$ and —N($CH_3$)S(=O)$C_6H_5$.

Sulfamyl: —S(=O)$NR^{N1}R^{N2}$, wherein $R^{N1}$ and $R^{N2}$ are independently amino substituents, as defined for amino groups. Examples of sulfamyl groups include, but are not limited to, —S(=O)$NH_2$, —S(=O)NH($CH_3$), —S(=O)N$(CH_3)_2$, —S(=O)NH($CH_2CH_3$), —S(=O)N$(CH_2CH_3)_2$, and —S(=O)NHPh.

Sulfonamino: —$NR^{N1}$S(=O)$_2$R, wherein $R^{N1}$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2CH_3$ and —N($CH_3$)S(=O)$_2$$C_6H_5$. A special class of sulfonamino groups are those derived from sultams—in these groups one of $R^1$ and R is a $C_{5-20}$ aryl group, preferably phenyl, whilst the other of $R^1$ and R is a bidentate group which links to the $C_{5-20}$ aryl group, such as a bidentate group derived from a $C_{1-7}$ alkyl group. Examples of such groups include, but are not limited to:

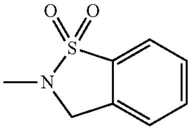

2,3-dihydro-tenzo[d]isothiazole-1,1-dioxide-2-yl

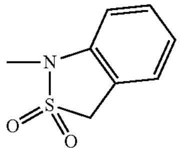

1,3-dihydro-benzo[c]isothiazole-2,2-dioxide-1-yl

-continued

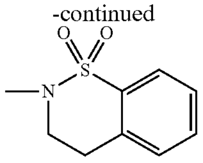

3,4-dihydro-2H-benzo[e][1,2]thiazine-1,1-dioxide-2-yl

Phosphoramidite: —OP($OR^{P1}$)—$NR^{P2}_2$, where $R^{P1}$ and $R^{P2}$ are phosphoramidite substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidite groups include, but are not limited to, —OP($OCH_2CH_3$)—N($CH_3$)$_2$, —OP($OCH_2CH_3$)—N(i-Pr)$_2$, and —OP($OCH_2CH_2CN$)—N(i-Pr)$_2$.

Phosphoramidate: —OP(═O)($OR^{P1}$)—$NR^{P2}_2$, where $R^{P1}$ and $R^{P2}$ are phosphoramidate substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidate groups include, but are not limited to, —OP(═O)($OCH_2CH_3$)—N($CH_3$)$_2$, —OP(═O)($OCH_2CH_3$)—N(i-Pr)$_2$, and —OP(═O)($OCH_2CH_2CN$)—N(i-Pr)$_2$.

In many cases, substituents may themselves be substituted. For example, a $C_{1-7}$ alkoxy group may be substituted with, for example, a $C_{1-7}$ alkyl (also referred to as a $C_{1-7}$ alkyl-$C_{1-7}$ alkoxy group), for example, cyclohexylmethoxy, a $C_{3-20}$ heterocyclyl group (also referred to as a $C_{5-20}$ aryl-$C_{1-7}$ alkoxy group), for example phthalimidoethoxy, or a $C_{5-20}$ aryl group (also referred to as a $C_{5-20}$aryl-$C_{1-7}$alkoxy group), for example, benzyloxy.

Preferred substituents for an aryl or alkyl group may include $C_{1-10}$ alkyl groups, $C_{5-20}$ aryl groups, hydroxyl, $C_{1-7}$alkoxy groups, nitro, amino, substituted amino (—$NR^{N1}R^{N2}$ as defined above) and halides.

Isomers, Salts, Solvates, and Protected Forms

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and I-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

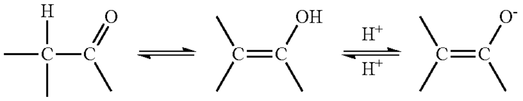

keto enol enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g. asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below. It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.,* 66, 1-19 (1977).

For example, if the compound is anionic, or has a functional group which may be anionic (e.g., —COOH may be —$COO^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulphuric, sulphurous, nitric, nitrous, phosphoric, and phosphorous. Examples of suitable organic anions include, but are not limited to, those derived from the following organic acids: acetic, propionic, succinic, glycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, phenylsulfonic, toluenesulfonic, methanesulfonic, ethanesulfonic, ethane disulfonic, oxalic, pantothenic, isethionic, valeric, lactobionic, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form", as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1999).

For example, a hydroxy group may be protected as an ether (—OR) or an ester (—OC(═O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(═O)$CH_3$, —OAc).

For example, an aldehyde or ketone group may be protected as an acetal or ketal, respectively, in which the carbonyl group (>C═O) is converted to a diether (>C$(OR)_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—$CH_3$); a benzyloxy amide (—NHCO—$OCH_2C_6H_5$, —NH-Cbz); as a t-butoxy amide (—NHCO—$OC(CH_3)_3$, —NH-Boc); a 2-biphenyl-2-propoxy amide (—NHCO—$OC(CH_3)_2C_6H_4C_6H_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO.).

For example, a carboxylic acid group may be protected as an ester for example, as: an $C_{1-7}$ alkyl ester (e.g. a methyl ester; a t-butyl ester); a $C_{1-7}$ haloalkyl ester (e.g., a $C_{1-7}$ trihaloalkyl ester); a tri$C_{1-7}$ alkylsilyl-$C_{1-7}$ alkyl ester; or a $C_{5-20}$ aryl-$C_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—$CH_2$NHC(═O)$CH_3$).

Prodrugs

It is contemplated that some of the active compounds of the invention act in the form of prodrugs, that means that they are metabolised in the body to the active form. Among these compounds are esters such as glyceryl tributyrate, glyceryl tripropionate, glyceryl tri(4-phenylbutyrate) and methyl 4-phenylbutyrate.

Further Aspects and Embodiments

In the following aspects or embodiments of the invention the compound of the invention is any as defined above e.g. as in formula Ia or formula I, or IIIa.

Preferably the compound is a butyric acid/butyrate derivative such as an acid salt, ester or amide such as is defined by any of formula IIa, IIb, IIc, IId, IIe.

Preferably it comprises at least one aryl substituent, which is preferably at $R^4$, such as is defined by any of formula IVb.

In particular aspects of the invention there are provided methods for treating, preventing or counteracting a microbial infection in a patient in need of the same, by administering to the patient an effective amount of a compound of the invention as described herein.

The effective amount is sufficient to demonstrate antimicrobial activity in vivo e.g. by stimulating (e.g. derepressing or inhibiting down-regulation of) synthesis of the cathelicidin LL-37. Stimulation may be towards, equal to, or above basal levels (i.e. normal levels in the absence of the infection).

By the term "antimicrobial activity" as used herein, is meant the ability to inhibit the growth of or actually kill a population of microbes which can be bacteria, viruses, protozoa or fungal microbes. Thus "antimicrobial activity" should be construed to mean both microbistatic as well as microbicidal activities. Antimicrobial activity should also be construed to include a compound which is capable of inhibiting infections, i.e. disease-causing capacity of microbes.

The compounds of the present invention exhibit an antimicrobial effect by stimulating the innate antimicrobial peptide defense system.

Generally the use of the present invention will be such as to lead to secretion of the relevant peptide same onto an epithelial surface (e.g. in the gastrointestinal tract). This in turn will lead to increased antimicrobial activity at the surface (and hence improvement of its barrier function) and treatment of the microbial infection and disease caused by it.

The microbial targets and diseases targeted by the present invention may be any believed to benefit therefrom, but a preferred target is infectious colitis e.g. as caused by *Clostridium difficile* colitis.

The compounds of the invention are particularly useful against infections of bacterial strains that are tolerant against conventional antibiotics. Nevertheless use of the compounds described herein in conjunction with conventional antibiotics may be preferred and forms one part of the present invention.

Other combination treatments of the present invention include the use of compounds described herein with other compounds believed to have antimicrobial effect.

These include: aminosterol type compounds, for example which include spermidine, spermine or other polyamines (see WO2000-09137); isoleucine or active isomers or analogs thereof (see US2002-0076393 or US2003-0109582 or U.S. Pat. No. 7,311,925); and vitamin D type compounds (see US20080038374 or WO/2008/073174). The disclosure of all these references, in respect of these compounds, their definition, and their provision, is hereby specifically incorporated herein by cross-reference.

Preferred dosages and dosage forms are described in more detail below. A preferred daily dosage may be between 250 μg to about 25 g, preferably up to around 5 g, more preferably less than 3 g per day, which may be split into doses given e.g. 1, 2 or 3 times daily.

Said compound is preferably administered in an oral dosage form such as but not limited to a tablet, a capsule, a solution, a suspension, a powder, a paste, an elixir, and a syrup. Other administration forms are also useful, these include but not are limited to topical administration forms, which are in particular useful against infections of the skin, these include for example creams, oils, lotions, and ointments. Yet further dosage forms include dosage forms for delivery to the respiratory system including the lungs, such as aerosols and nasal spray devices.

Aspects of the invention include a method for treating, preventing or counteracting microbial infections, including bacterial, viral, fungal and parasitic infections (also including infections by bacterial strains resistant to currently used antibiotics), by administering a medicament comprising a secretagogue-effective amount of at least one compound of the invention as defined above.

In yet a further aspect, the invention provides a pharmaceutical composition for use in the methods described herein e.g. for treating, preventing or counteracting a microbial infection, including the above mentioned types, comprising an active ingredient being at least one compound of the invention, and typically at least one pharmaceutically acceptable excipient.

In yet a further aspect, the invention provides use of compounds of the invention in the preparation of a medicament for use in the methods described herein.

Some of these aspects and embodiments will now be discussed in more detail:

Secretion of Host Defense Peptides

The gastrointestinal tract (GI tract) of mammals is covered by a continuous sheet of epithelial cells that is folded into villus projections and crypts. Within the base of the crypts, where the stem cells of the GI tract can be found, there are specialized, granular cells called Paneth cells. Both enterocytes and Paneth cells produce antimicrobial peptides. The enterocytes synthesize and secrete antimicrobial peptides into the gut lumen both constitutively and upon induction. The Paneth cells at the base of the intestinal crypts, secrete alpha-defensins into the cryptal well, resulting in concentrations estimated at mg/mL levels, which eventually flush into the gut lumen.

Both systems contribute to bowel health. In children and adults suffering from diarrhea caused by *Shigella*, synthesis of the cathelicidin LL-37 and the colonic enterocyte beta-defensin HBD-1 is markedly depressed; expression recovers in time during resolution of the illness. Similarly, mice which lack the proteolytic enzyme required for processing cryptdins (the murine Paneth cell alpha-defensins) lack functional cryptdins and exhibit increased susceptibility to orally administered *Salmonella*.

Other epithelial surfaces of the mammalian body also have such host defense secretion systems, including but not limited to the cornea, the lung, the kidney and the skin.

The use of the compositions and methods of the present invention result in the stimulation of epithelial cells and Paneth cells of the gastrointestinal tract and other epithelial surfaces of man and in other animals to secrete large quantities of naturally occurring broad-spectrum antimicrobial agents, including antimicrobial peptides such as defensins, cryptdins, LL-37, HBD1, and HBD2, and antimicrobial proteins such as lysozyme, transferrin, lactoferrin, phospholipases, and SLPI (secretory leukocyte protease inhibitor). The substances stored by the Paneth cells exhibit activity against a wide range of infectious agents including bacteria, protozoa, viruses, and fungi.

The epithelial cells targeted by the present invention may be any of these. Preferably however the invention is utilise for the treatment of microbial infections of the GI tract.

Microbial Infections and Diseases

As mentioned, an important aspect of the invention provides methods for treating, preventing or counteracting microbial infections by administering a medicament comprising a secretagogue-effective amount of at least one compound of the invention.

In useful embodiments, infections and other conditions that benefit from treatment according to the invention are in particular those relating to organs having epithelial surfaces with host defense peptide secretion systems such as the above mentioned.

Such infections, conditions and diseases include but are not limited to traveller's diarrhoea, endemic diarrhoea, dysentery, viral gastroenteritis, parasitic enteritis, Crohn's disease, ulcerative colitis, irritable bowel syndrome, precancerous states of the gastrointestinal tract, cancer of the gastrointestinal tract, diverticulitis, post-antibiotic diarrhoea, *Clostridium difficile* colitis, lactose intolerance, flatulence, gastritis, esophagitis, heartburn, gastric ulcer, ulcers associated with *Helicobacter pylori*, duodenal ulcer, short bowel syndrome, dumping syndrome, gluten enteropathy, or food intolerance.

Also included in the methods of the inventions are infections of the skin, including but not limited to boils, carbuncles, furuncles, cellulitis, abscesses, impetigo, and erysipelas; infections of the eye including but not limited to conjunctivitis, stye, blepharitis, cellulitis, keratitis, corneal ulcer, trachoma, uveitis, canaliculitis and dacryocystitis, infections to the respiratory system and infections in the kidneys. Also included are infections caused by bacterial strains resistant to classical antibiotic treatment, including infections by multidrug resistant strains.

A preferred target for the present invention is infectious colitis. As is well known in the art, microbial species causing this include *Yersenia enterocolitica, Salmonella, Shigella, Campylobacter, Clostridium* and *E. Coli*. Some bacteria, such as *Clostridium difficile*, may elaborate a toxic substance that leads to the development of pseudomembranous colitis.

The compounds of the invention are particularly useful against infections of bacterial strains that are tolerant against conventional antibiotics, and it follows from the secretagogue action of the compounds in the context herein, that it is not foreseen that bacterial strains can develop resistance against treatment in accordance with the invention.

As illustrated in the accompanying Examples, selected representative compounds have been tested and found to exhibit the desired activity.

Combination Treatments

As noted above, use of the use of the compounds described herein in conjunction with conventional antibiotics may be preferred and forms one part of the present invention. Example antibiotics include Penicillins, Penicillin G, Phenoxymethyl—penicillin, Flucloxacillin, Amoxycillin, Metronidazole, Cefuroxime, Augmentin, Pivmecillinam, Acetomycin, Ciprofloxacin and Erythromycin. Where these specific antibiotics are named, it will be appreciated that commonly available analogs may be used.

As demonstrated in the accompanying Examples (see Examples 4-6) it has been found that a combinatorial effect is achieved when compounds of the invention are administered together with vitamin D. Accordingly, the invention also encompasses the above methods, further comprising the co-administration of vitamin D, with one or more compounds of the invention. Other compounds which may be co-administered include aminosterol type compounds; isoleucine or active isomers or analogs thereof; vitamin D type compounds.

Also provided are pharmaceutical compositions comprising, in addition to one or more of the compounds of the invention, vitamin D or one of the other aforementioned compounds as a further ingredient. Such compositions can be formulated in any of the above mentioned formulations and dosage forms.

Oral dosage forms are preferred, as described below.

Preferred Dosages

In the methods and compositions of the present invention, the active compound is administered/present in an amount which is effective to stimulate and/or activate this system. Such amount is also referred to herein as a "secretagogue-effective" amount, where the term secretagogue refers to a substance which increases the levels of active antimicrobial peptides in epithelial surfaces.

As noted hereinbefore, PBA has previously been marketed for treatment of hyperammonaemia related to hereditary urea cycle disorders. According to the SPC of Buphenyl (tablet or powder) the drug is dosed at 9.9 to 13.0 $g/m^2$/day divided into three portions. This amounts to 16-23 g daily, or ca. 5.5 to 8.0 g three times daily.

In different studies, topical dosages for PBA used in various studies ranged from 528 mg/day to 1.12 g/day, which corresponds to 35-60% of the normal daily intracolonic production of butyrate. None of these studies reported any adverse effect or reactions. According to one study, daily oral dose of 4 g of sodium butyrate given as colonic-targeted tablets for 6-weeks in IBD patients and was also found safe and well tolerated without any adverse effects.

Rabbit studies performed at ICDDRB in Dhaka (see below) showed that dosing about 7.5-22.5 mg/kg was sufficient for therapeutic effect in shigellosis. Scaling this dose to a 70 kg human suggests that a maximally 720 mg daily dose would be effective for the treatment of, for example, shigellosis.

Based on these examples it will be appreciated that a practical upper limit for treatment would be of the order of 20 g/daily (based on urea cycle treatment) and the lower limit may be expected to be lower than 700 mg, e.g. equal to or around 600, 500, 400, 300, 200, 100 mg daily. Potentially even lower amounts may be utilised e.g. 90, 80, 70, 60, 50, 40, 30, 20, 10, 9, 8, 7, 6, 5, 4, 3, 2, or 1 mg.

It will nevertheless be understood that the suitable amount of the compound to be administered can vary depending on the selected specific compound(s), the specific location of the infection and condition(s) to be treated and/or prevented. In some embodiments, the amount to be administered can be in the range of about 10 μg to about 25 g. A suitable dosage form can be selected and formulated accordingly. For example, for treatment of diseases and conditions in the gastro-intestinal system a dose in the range of 250 μg to about 25 g may be suitable, including the range of about 1 g to about 25 g, e.g. in the range of about 1 g to 10 g, such as about 1 g, 2 g, 5 g or 10 g.

All dosages may be split or given e.g. 1, 2 or 3 times daily.

Administration and Formulation

Preferably, the medicament is administered orally but other administration routes are within the scope of the invention and may be more suitable for certain conditions. Such other administration routes include topical, buccal nasal, parenteral, including rectal and vaginal administration.

Inhaled dosage forms include aerosol, inhaler & metered dose inhaler. Ophthalmic dosage forms include eye drops (solution or suspension), ophthalmic gels, and ophthalmic ointments. Otic dosage forms include ear drops (solution or suspension). Rectal dosage forms include enema and suppository. Vaginal dosage forms include douches and pessaries (vaginal suppositories) and vaginal tablets.

Examples of suitable formulations for topical use include creams, ointments, gels, or aqueous or oily solutions or suspensions. Parenteral administration can be accomplished for example by formulating the compound as a sterile aqueous or oily solution for intravenous, subcutaneous, or intramuscular dosing or as a suppository for rectal dosing.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

The compositions can be formulated in various suitable forms, depending on which conditions they are primarily aimed at. In certain embodiments, the compositions are for oral administration. Such compositions include but are not limited to tablets, capsules, a solution, a suspension, a powder, a paste, an elixir, or a syrup.

Compositions may be delayed-release or colonic-targeted compositions such as are well known in the art.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions

Another aspect of the invention relates to a pharmaceutical composition for treating, preventing or counteracting any of the above mentioned conditions or diseases. The compositions comprise at least one of the compounds described herein together with at least one pharmaceutically acceptable excipient.

The oral composition of the invention may be formulated for delayed and/or extended release and may be enteric coated by means well known to the skilled person, to be released in the lower intestinal tracts.

Functional Foods

It will also be appreciated, in particular when it is desired to administer a large amount of active compound, such as, in the range of 1-25 g that the compounds of the invention can be (isolated and then) formulated and comprised in functional food or feed products. Such functional food products include but are not limited to fermented food products including fermented bean products, e.g. soy bean products such as tempeh, products from fermented oat, germinated barley, and similar products. Such products, generally produced by microbial fermentation which breaks down betaglucans, will have a natural content of short chain fatty acids that can boost the effect of the compounds of the present invention. The form of functional food product in accordance with the invention can be any form suitable for the chosen food type, including crackers, pastry, spread or paste, a purée, a jelly, a yoghurt, a drink concentrate, or any other suitable food product in which the selected active compound(s) can be readily formulated in.

Other Species

The methods and compositions of the present invention have application in the treatment of both humans as well as other animals, including veterinary and animal husbandry applications for companion animals, farm animals, and ranch animals. These applications include but are not limited to treating, preventing or counteracting diseases and conditions in dogs, cats, cows, horses, deer and poultry including hen, turkey ducks, geese; as well as in household pets such as birds and rodents. For large animals, a suitable dose can be larger than the above mentioned amounts.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, in as much as it may be used by those skilled in the art to carry out the invention, is hereby specifically incorporated herein by cross-reference.

FIGURES

FIG. 1: Fold-induction of CAMP mRNA (encoding LL-37) levels in lung epithelial cells (VA10), upon treatment with different agents of the invention. Column c represents a control (untreated cells), Column 3 represents a positive control of vitamin D3 (1,25-dihydroxyvitamin $D_3$ or 1,25(OH) $2D_3$) treated cells, column 1 is sodium butyrate and column 2 is sodium 4-phenylbutyrate treated cells. Cells were harvested 24 hours after sodium 4-phenylbutyrate and vitamin D stimulation, and mRNA was isolated. Real time reverse transcription PCR results show how expression of the human cathelicidin gene is affected by sodium 4-phenylbutyrate and vitamin D treatment.

Figure 2:
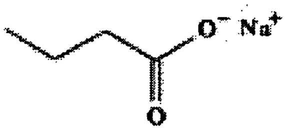
Figure 2:
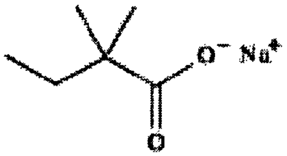
Figure 2:
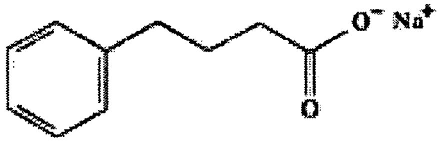
Figure 2:
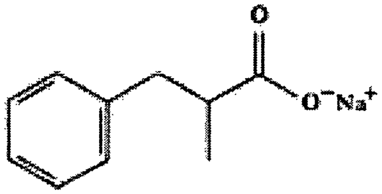
Figure 2:
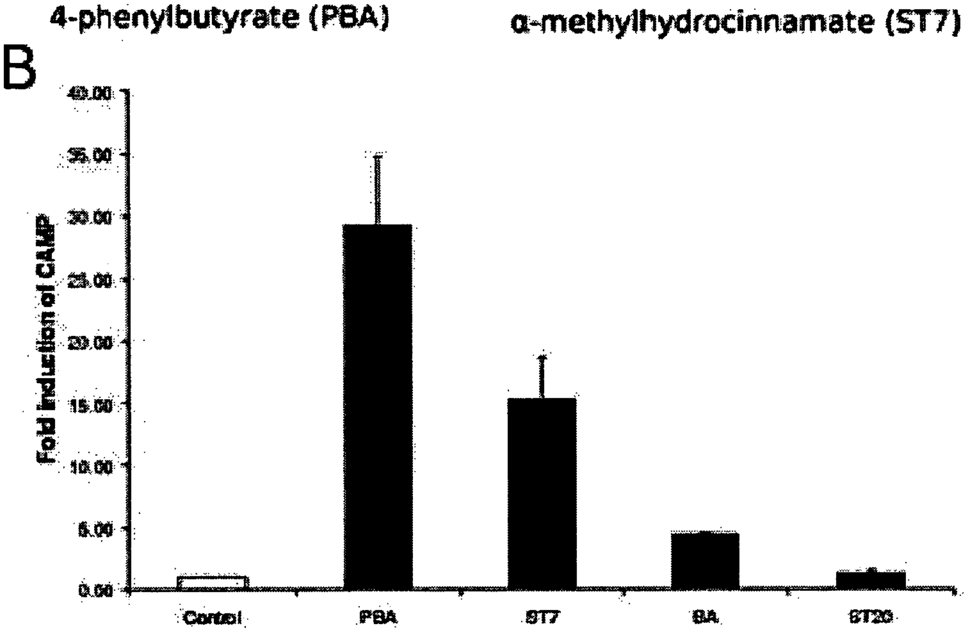

FIG. 2: Induction of CAMP mRNA expression by butyrate (BA) and PBA derivates. A) Structures of utilized chemicals butyrate (BA) 4 mM, 4-phenyl butyrate (PBA) 4 mM, α-methyl hydrocinnamate (ST7) 4 mM, and 2,2-dimethyl-butyrate (ST20) 4 mM. B) Induction of CAMP mRNA expression by indicated chemicals for 24 hours.

Figure 3:
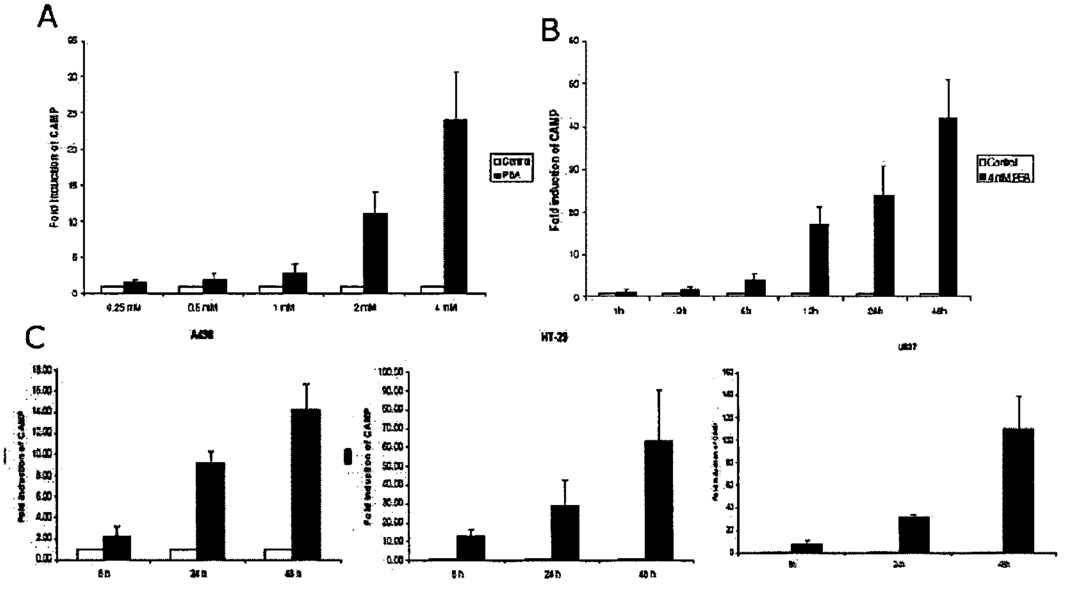

FIG. 3: Induction of CAMP gene mRNA expression by PBA. A) VA10 cells were stimulated with the indicated concentrations of PBA or solvent (Control) for 24 hours. B) VA10 cells were stimulated with 4 mM PBA or treated with solvent alone and harvested after the indicated period of time. C) A498, HT-29 and U937 cells were stimulated with 4 mM PBA or solvent only and harvested after the indicated period of time. CAMP mRNA levels were determined by real time RT-PCR. Individual samples were normalized to total RNA input. Results were normalized to expression in control samples where controls were given the arbitrary value of one. The normalized data is plotted as mean+SE from at least three independent experiments.

Figure 4:
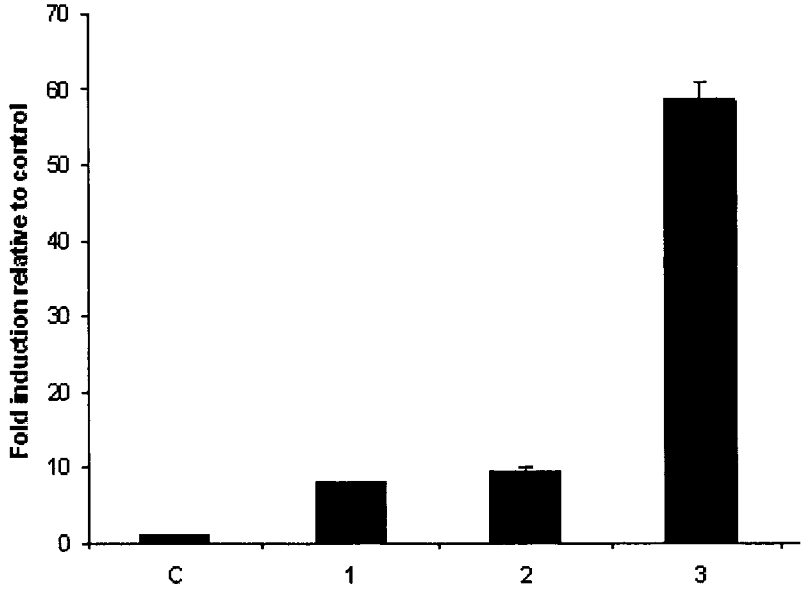

FIG. 4: Combinatorial effects of vitamin D and sodium 4-phenylbutyrate stimulation on CAMP mRNA expression in lung epithelial VA10 cells, determined as described above for FIG. 1. The columns are as follows: C=control; 1=sodium 4-phenylbutyrate alone; 2=vitamin D alone; 3=treatment of sodium 4-phenylbutyrate together with vitamin D.

Figure 5:
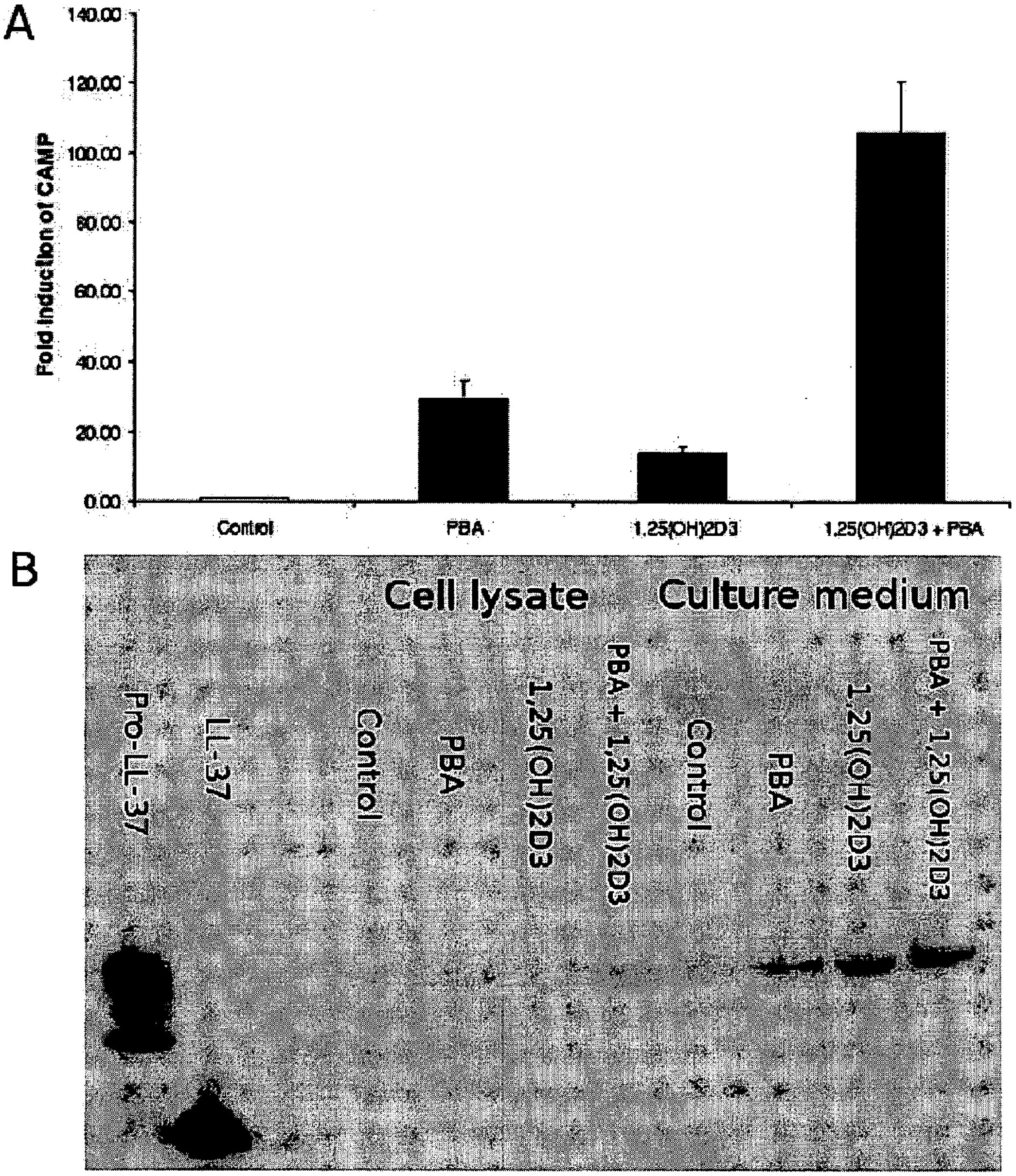

FIG. 5: Further demonstrations of synergetic induction of CAMP mRNA and pro-LL-37 expression by PBA (4 mM) and $1,25(OH)_2D_3$. (20 nM) A) VA10 cells were stimulated with PBA (4 mM), $1,25(OH)_2D_3$ (20 nM) or solvent (Control) for 24 hours. CAMP mRNA levels were determined by real time RT-PCR. Individual samples were normalized to total RNA input. Results were normalized to expression in control samples where controls were given the arbitrary value of one. Normalized data is plotted as mean+SE from three independent experiments. The differences observed are significant ($P<0.05$). B) VA10 cells were stimulated with PBA (4 mM), $1,25(OH)_2D_3$ (20 nM) or solvent (Control) for 24 hours. Total cell lysates and supernatants analyzed by Western blot for LL-37. One representative blot out of three is shown.

Figure 6:
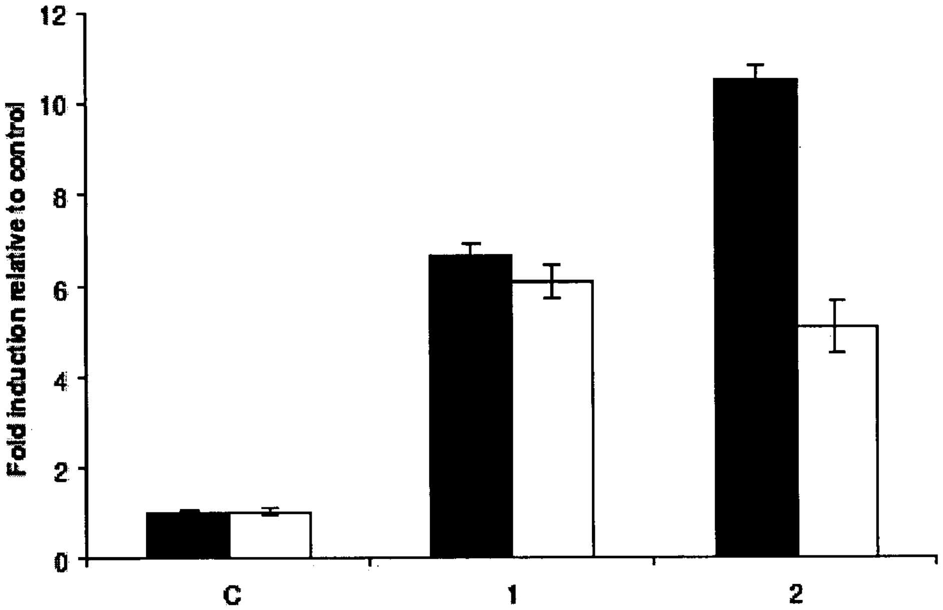
Figure 6:
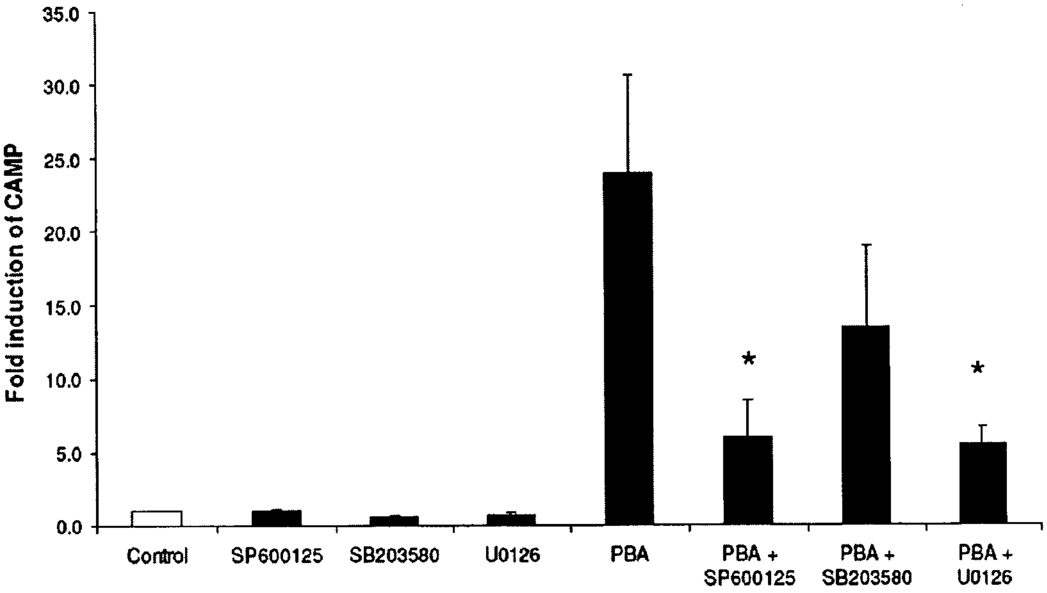

FIG. 6A: Induction of the gene encoding LL-37 with sodium 4-phenylbutyrate and vitamin D is affected by the inhibitor U0126 which inhibits the MEK/ERK kinase pathway. C=control; 1=sodium 4-phenylbutyrate alone; 2=vitamin D alone. The open columns represent treatment with the inhibitor U0126. The black columns show treatment without the inhibitor. This indicates that the signaling pathways are affected differently by vitamin D and phenylbutyrates.

FIG. 6B. Further demonstration of inhibition of PBA induced CAMP gene expression by MAP kinase inhibitors as shown in the Figure, VA10 cells were treated with 4 mM PBA in the presence or absence of 20 μM of the indicated inhibitors. CAMP mRNA levels were determined by real time RT-PCR. Individual samples were normalized to total RNA input. Results were normalized to expression in control samples where controls were given the arbitrary value of one. Normalized data is plotted as mean+SE from three independent experiments. *: $P<0.05$; : $P<0.01$; *: $P<0.001$ FIG. 7: Immunohistochemistry showing that CAP-18 (the rabbit homologue to LL-37) is expressed in surface epithelial cells of healthy rabbits, that *Shigella* infection results in downregulation of the peptide and that this downregulation can be counteracted by oral intake of tributyrylglycerol.

Figure 8:
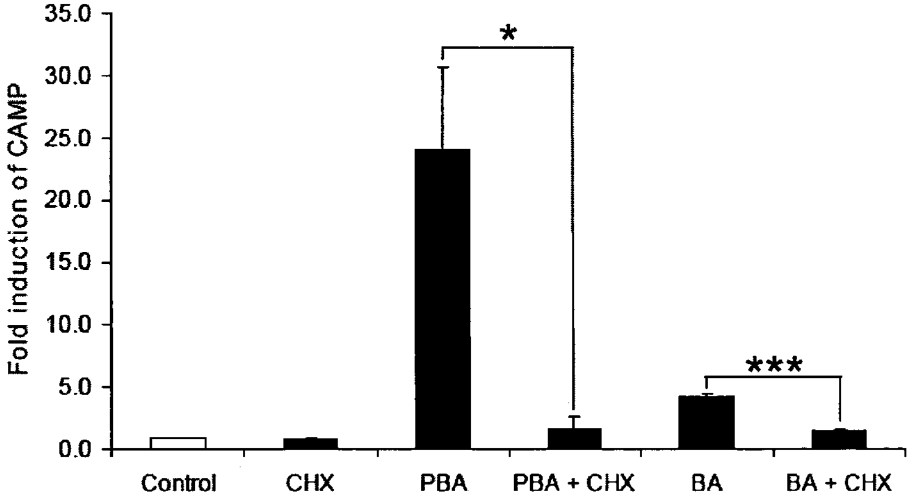

FIG. 8: Inhibition of PBA induced CAMP gene expression by cycloheximide shows that translation is necessary. VA10 cells were treated with 4 mM PBA or butyrate (BA) in the presence or absence of 20 μg/ml cycloheximide. CAMP mRNA levels were determined by real time RT-PCR. Individual samples were normalized to total RNA input. Results were normalized to expression in control samples (solvent) where controls were given the arbitrary value of one. Normalized data is plotted as mean plus standard error of the mean from at least three independent experiments. *: $p<0.05$; : $p<0.01$; *: $p<0.001$.

Figure 9:
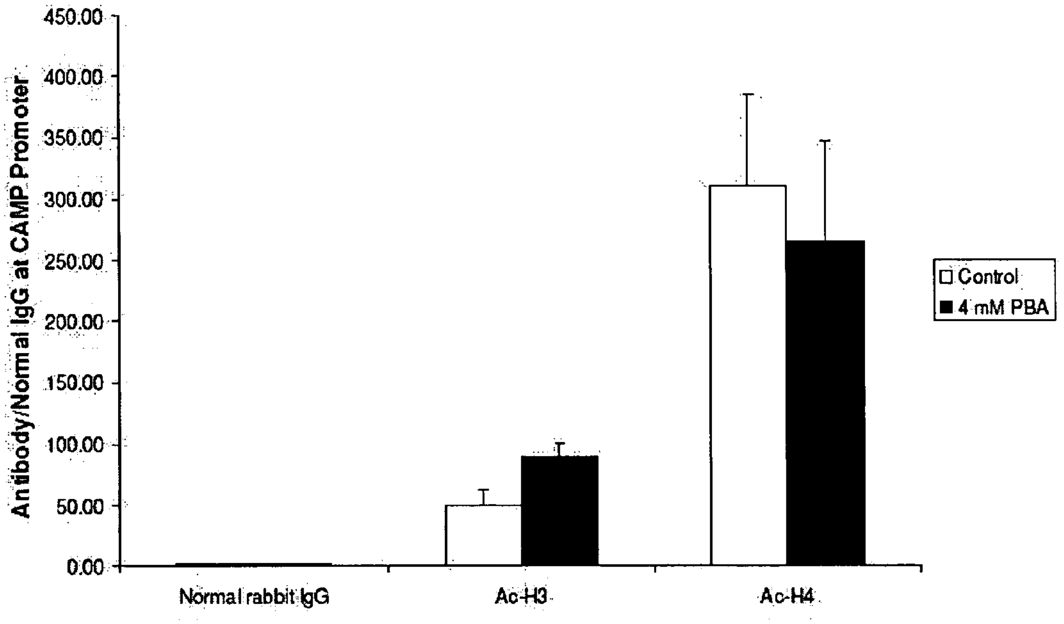

FIG. 9: VA10 cells were stimulated with 4 mM of PBA or solvent alone (Control) for 24 hours. Acetylation of histone H3 and H4 was analyzed by quantitative ChIP using antibodies against the respective acetylated histones. Results were normalized to normal rabbit IgG and total input and plotted as fold precipitation over IgG. Normalized data is plotted as mean+SE from independent experiments (n=3). No significant differences were observed in acetylation of histones.

Figure 10:
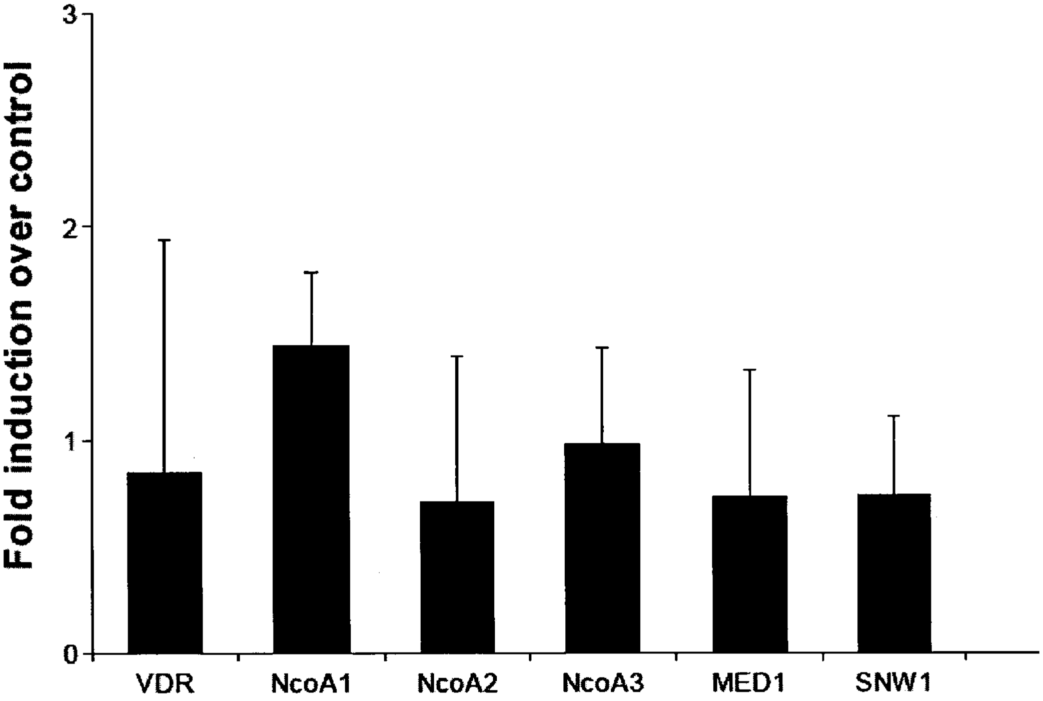

FIG. 10: PBA induced expression does not involve the co-activators of VDR. VA10 cells were stimulated with 4 mM of PBA or solvent alone (Control) for 24 hours. mRNA levels of the respective VDR co-activators were determined by real time RT-PCR. Individual samples were normalized to total RNA input. Results were normalized to expression in control samples where controls were given the arbitrary value of one. Data is normalized to control and plotted as mean+SE from three independent experiments.

Figure 11:
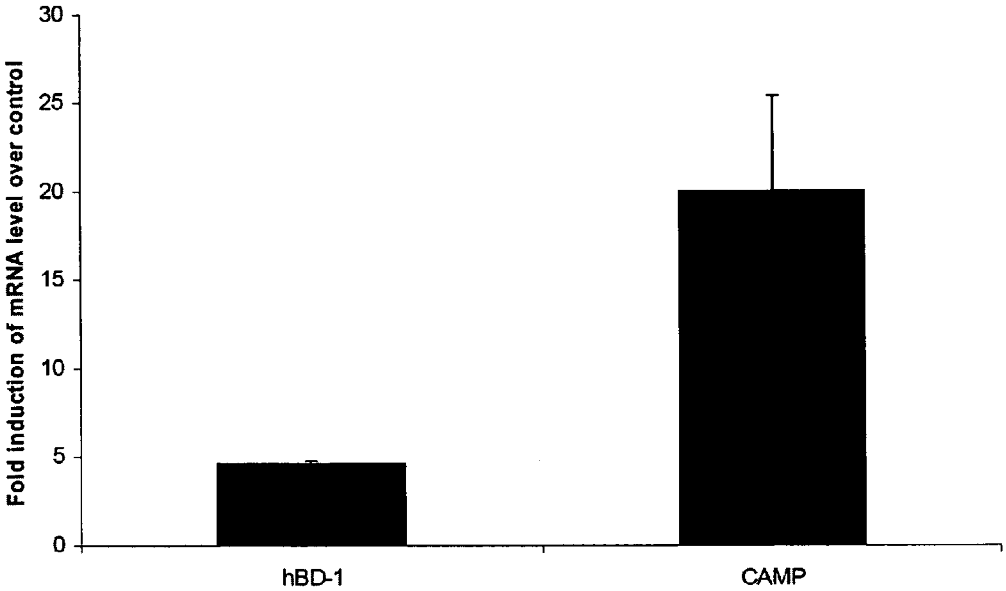

FIG. 11: Induction of hBD-1 mRNA expression by PBA. VA10 cells were stimulated with 4 mM of PBA or solvent alone (Control) for 24 hours. hBD-1 mRNA levels were determined by real time RT-PCR, CAMP induction shown for comparison. Individual samples were normalized to total RNA input. Results were normalized to expression in control samples where controls were given the arbitrary value of one. Data is normalized to control and plotted as mean+SE from at least three independent experiments.

Figure 12:
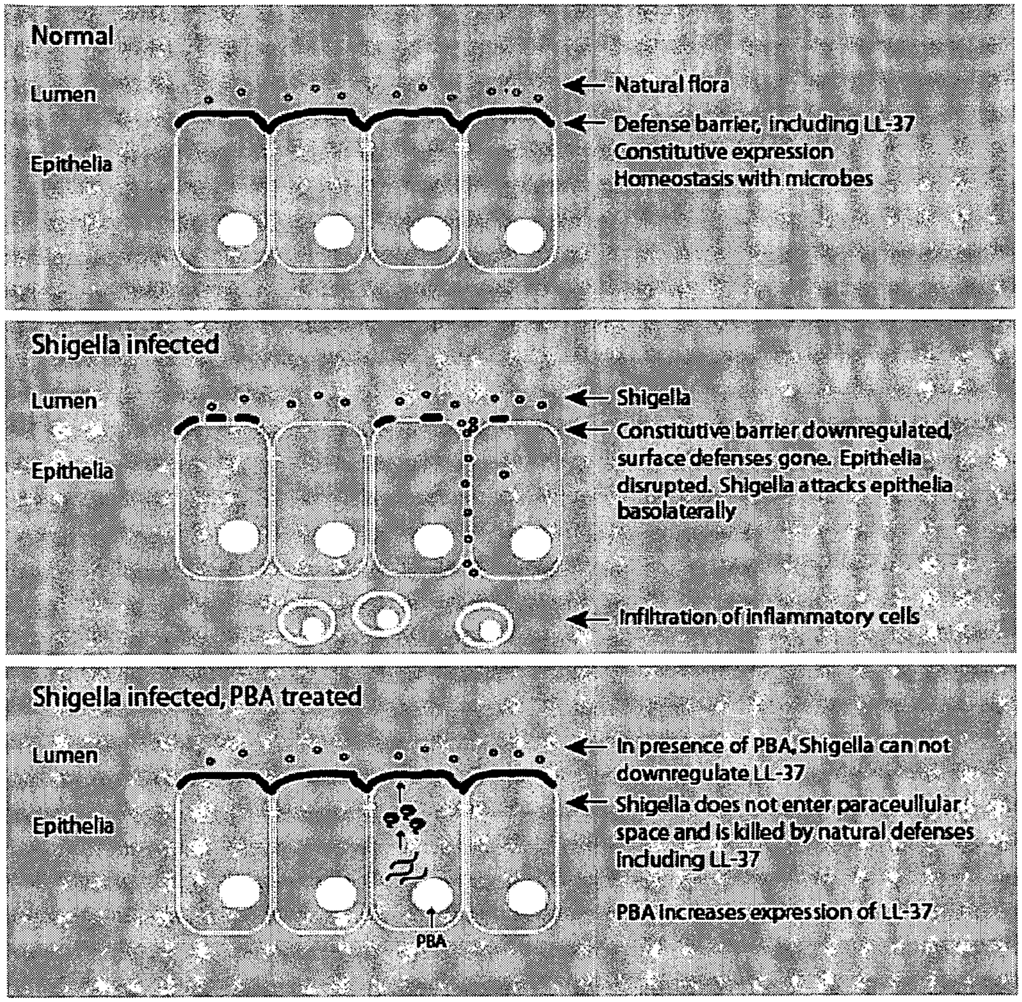

FIG. 12: Schematic illustration of proposed mechanism for action of PBA treatment in *Shigella* infected epithelia.

EXAMPLES

Example 1

LL-37 expression in lung epithelial cells treated with different agents Lung epithelial cells (VA 10) were grown to confluency under standard conditions and the agents to be tested added at the indicated concentrations (see below). mRNA was isolated 24 hours after treatment and measured by real time reverse transcription PCR.

Results are shown in FIG. 1, where column C represents control (untreated cells), column 3 represents a positive control of vitamin D3 (1,25-dihydroxyvitamin $D_3$ or 1,25(OH) 2D3) (100 nM) treated cells, column 1 is sodium butyrate (2 mM) and column 2 is sodium 4-phenylbutyrate (2 mM) treated cells.

The results show that sodium 4-phenylbutyrate is a more effective inducer of LL-37 mRNA expression than butyrate or vitamin D in VA10 cells, but does not have does not have the foul smell associated with butyrate. Prior to our studies there were no compounds known to induce LL-37 to the same degree as butyrate let alone without the smell and taste problem. It is particularly surprising that the deviation from the structure of butyrate can be as substantial as adding an aromatic ring (i.e. doubling the molecular weight). In the light of the present disclosure it may therefore be concluded that that butyrate derivatives, such as aromatic derivatives, will also be active.

In a further experiment, the ability of two other PBA analogs to induce CAMP gene expression was tested (see FIG. 2). VA10 cells were stimulated with 4 mM of α-methylhydrocinnamate (ST7), a PBA analog or 2,2-dimethylbutyrate (ST20), a butyrate analog. After 24 hours of incubation, total RNA was isolated from the cells and CAMP mRNA expression levels analyzed by real time RT-PCR. ST7 significantly increased CAMP mRNA expression, while ST20 stimulation had no apparent effect on CAMP mRNA expression levels. Thus it can be seen that quaternary carbon atoms, at least proximal to the carboxyl group, would appear to be undesirable. Conversely, in aryl-butyrate derivatives, it appears that analogs including different chain or branched chains, remain active.

Real Time PCR

Six-well plates were seeded with $1.0\times10^6$ cells per well and grown for two days. Medium was then exchanged and different wells were left untreated, supplemented with 2 mM sodium butyrate or 2 mM sodium 4-phenylbutyrate. The cells were incubated for 48 h and total RNA was prepared using the RNEasy kit (Qiagen). Total RNA concentrations were measured using the Quant-iT RiboGreen RNA assay kit (Invitrogen). Superscript III first-strand synthesis system (Invitrogen) was used to synthesize cDNA using random primers according to the protocol of the manufacturer. The expression of the CAMP gene, encoding LL-37 was analyzed on the 7500 Real Time PCR System (Applied Biosystems) using the fluorescent probe (5"-6-FAM-TGTTATCCTTATCA-CAACTGAT-3' with MGB quencher) and forward and reverse primers specific for the CAMP cDNA (5'-ACCCAG-CAGGGCAAATCTC-3' and 5'-GAAGGACGGGCTGGT-GAAG-3', respectively). Results were normalized to total RNA quantity, presented as relative fold induction of untreated control cells.

Example 2

LL-37 Expression in Lung Epithelial Cells Treated with Different Dose of Sodium 4-Phenylbutyrate FIG. 3 shows the dose-response of CAMP mRNA expression in VA10 lung epithelial cells upon treatment with increasing concentrations of sodium 4-phenylbutyrate. To determine time and dose dependence of PBA induced expression of CAMP mRNA, VA10 cells were stimulated with 4 mM PBA over different time points and with different concentrations for 24 hours. Total RNA was isolated from the cells and CAMP mRNA expression levels analyzed by real time RT-PCR. Increase of CAMP mRNA expression was dependent on PBA dose and increased over time.

In earlier experiments it appeared that at higher concentrations, which were non-physiologically relevant (8 mM) the response ceased to be dose-dependent (results not shown).

In earlier experiments in which controls were not measured at the relevant time points, artifacts were seen after long incubations (48 hours; results not shown). Therefore in the experiment shown, controls were measured at the relevant time point and normalised to 1.

The example indicates that successful treatment can be envisaged with a once-daily dosage regimen.

Example 3

Induction of CAMP Gene Expression by PBA in Other Cell Lines

In order to investigate the effect of PBA on other cell lines, HT-29 (Human colonic adenocarcinoma cell line), A497 (Human renal carcinoma cell line) and U937 (Human leukemic monocyte lymphoma cell line) were stimulated with 4 mM PBA for 8, 24 and 48 hours. Total RNA was isolated from the cells and CAMP mRNA expression levels analyzed by real time RT-PCR. CAMP mRNA expression was significantly increased in all cell lines tested (FIG. 3C).

Example 4

Synergistic Effects of Sodium 4-Phenylbutyrate and Vitamin D on LL-37 Expression in Lung Epithelial Cells A further test shows that sodium 4-phenylbutyrate and vitamin D have combinatorial effects on CAMP mRNA expression. VA10 lung epithelial cells were grown as before and treated with sodium 4-phenylbutyrate alone at 2 mM vitamin D alone at 100 nM, and both together, at 2 mM and 100 nM respectively. Treatment with butyrate (at 2 mM) was included as control. Cells were harvested at different time-points and mRNA was isolated and analysed with real-time reverse transcription PCR. Treatment with both sodium 4-phenylbutyrate and vitamin D clearly show combinatorial effects on mRNA expression level as the effects of the combination are 6-fold higher than of either chemical alone.

In FIG. 4, column c shows CAMP mRNA levels in the control (untreated cells), column 1 represents treatment with sodium 4-phenylbutyrate alone, column 2 shows treatment with vitamin D alone, and column 4 shows the treatment of sodium 4-phenylbutyrate together with vitamin D.

This is further shown in FIGS. 6A and 6B. VA10 cells were incubated with a low dose of 20 nM of $1,25(OH)_2D_3$ and 4 mM PBA together and with the respective compounds alone. Expression of CAMP mRNA was found to be higher than the added fold induction of PBA and $1,25(OH)_2D_3$, indicating a synergistic effect (FIG. 5).

Example 5

Stimulation by Sodium 4-Phenylbutyrate and Vitamin D Acts Through Different Signaling Pathways Epithelial lung cells were treated with sodium 4-phenylbutyrate or vitamin D. For each agent two samples were treated, with and without MAP kinase inhibitor U0126 (concentration of 20 μM) which is specific for inhibiting MEK1 and MEK2 protein kinases.

Results are shown in FIG. 6A, where column C represents control (untreated cells), column 1 shows treatment with sodium 4-phenylbutyrate at 2 mM, and column 2 shows treatment with vitamin D (100 nM) for 24 h. The open columns represent treatment with the MAP kinase inhibitor U0126, whereas the black columns show treatment without the inhibitor.

The results shown indicate that different signaling pathways are involved in the induction by sodium 4-phenylbutyrate and vitamin D; this may explain the combined effects of the chemicals on the induction of the CAMP gene.

The effect of inhibitors for c-Jun N-terminal kinase (JNK), p38 kinase and extracellular signal-regulated kinase ½ (ERK½) on PBA induced CAMP gene expression were also investigated as shown in FIG. 6B. One hour prior to stimulation with 4 mM PBA, VA10 cells were pre incubated with 20 μM SP600125, SB203580 or U0126 to inhibit the respective kinases. After 24 hours of incubation, total RNA was isolated and analyzed by real time RT-PCR for CAMP mRNA. Inhibitors for the ERK½ and JNK pathways significantly reduced PBA induced CAMP gene expression.

Example 6

*Shigella* Infected Rabbits Treated with Glyceryl Tributyrate

It has been confirmed by immunohistochemistry that CAP-18 (the rabbit homologue to LL-37) is expressed in surface epithelial cells of healthy rabbits (FIG. 7A) and that *Shigella* infection results in downregulation of peptide production (FIG. 7B). Furthermore, upon treatment with tributyrylglycerol, the downregulation of gene expression by *Shigella* is reverted and/or prevented (FIG. 7C).

Animal model: Inbred New Zealand White rabbits of either gender weighing 1.8 to 2 kg were used for the study. The animals were individually caged in a room maintained at 22-25° C. Before inclusion in the study, health status of the rabbits was determined by physical examination, culture of stool and rectal swab specimens and fecal parasitic examination. Healthy coccidia-free rabbits that were also free of enteric pathogens (e.g. *Salmonella, Shigella, Vibrio cholera*) were studied. Rabbits were infected with *Shigella* and divided into two groups, one group was treated orally with glyceryl tributyrate and the other with saline. Expression of the CAP-18 peptide and its proform in colonic and rectal tissue specimens were analyzed in healthy rabbits, in untreated infected rabbits, in infected and healthy rabbits treated with glycerol tributyrate. For analyses of toxicity effects of glycerol tributyrate healthy rabbits were also treated with this compound.

Bacterial strain and inoculum preparation: The *Shigella flexneri* 2a strain was isolated from stool of a patient. The strain was positive for the Serény test and Congo red binding, reflecting invasive properties (Berkhoff, H. A. and Vinal, A. C., 1986, Avian Dis. 30, 117-121)) From this stock, bacteria were subcultured on trypticase soya agar (TSA; Becton Dickinson, Sparks, Md.) plates and cultured overnight at 37° C. Three to five smooth colonies were inoculated in trypticase soya broth and cultured for 4 h with shaking at 37° C. The broth was then washed in normal saline at 7000 rpm for 10 min and bacterial pellet was suspended in normal saline to a concentration of $1\times10^9$ cfu in 7 mL that were given to the rabbits.

A non-surgical rabbit model of shigellosis was used in this study as described previously with slight modifications (Etheridge, M. E. et al., 1996, Lab. Anim. Sci. 46, 61-66). Briefly, rabbits were fasted for 36 hours and given a single oral dose of a tetracyclin hydrochloride (250 mg/kg; Novartis, Dhaka, Bangladesh) suspension. After that, rabbits were anesthetized with sodium pentobarbitol (33 mg/kg; Sigma, Chemical Co, St Louis, Mo.) and given 37.5 mg/kg weight of G-cimetidine (Gonoshasthoya Pharmaceuticals, Dhaka, Bangladesh) intravenously via the marginal car vein to inhibit gastric secretion. Fifteen minutes later, 7 ml of 5% sodium bicarbonate solution was administered orally with a sterile plastic feeding tube (3.33×465 mm, Tycohealthcare Ireland Ltd., Tullamore, Ireland), which was followed 15 minutes later by a second 15-ml dose of 5% sodium bicarbonate solution and a 7-ml dose of the bacterial suspension ($10^9$ cfu in 7 ml normal saline (0.9% w/v, pH 7.2)) immediately thereafter. Twenty minutes after inoculation of the bacterial suspension, 7 ml of Loperamide HCl (0.02 mg/kg body weight) in normal saline was introduced orally to reduce intestinal motility. Thereafter, rabbits were allowed to eat and drink regular food. Usually rabbits developed dysentery within 24 hours of bacterial inoculation. Time of bacterial inoculums was considered as 0 hr. After development of dysenteric symptoms, rabbits were given glyceryl tributyrate (47 μmol/kg body weight, i.e., 140 μmol butyrate equiv./kg) by an orogastric feeding tube twice daily at twelve hours interval for 3 days. Four days after bacterial inoculation, rabbits were given an overdose of intravenous sodium pentobarbitol (66 mg/kg; Sigma) for euthanasia.

To evaluate the presence of the CAP-18 peptide immunohistochemical staining was performed by using the chicken polyclonal antibody specific to CAP-18 (Innovagen). Briefly, paraffin sections were deparaffinized, hydrated and given microwave treatment in retrieval buffer (Dako laboratories A/S, Glostrup, Denmark) for 12 minutes followed by washing in phosphate buffer (pH 7.2). After cooling, endogenous peroxidase activity was quenched and sections were incubated overnight with the CAP-18-specific antibody (2 μg/ml) at room tempture. After washing, sections were incubated with horse-radish-peroxidase conjugated donkey anti-chicken antibody (1:200; Jackson ImmunoResearch Laboratories, Inc.) for 1 hr at room temperature. This was followed by washing and development of the color was with diaminobenzidine (DAB, brown). As a control, specific antibodies were replaced by irrelevant isotype-matched-antibodies. In addition, synthetic CAP-18 was incubated at 10-fold higher concentration with the CAP-18 antibody overnight at 4° C. and the mixture was used as above for immunostaining. This served as control for the specific staining. After counterstaining in hematoxylin and eosin, slides were mounted in paramount (BDH Chemicals, Poole, England).

Clinical recovery of the rabbits from shigellosis was established by disappearance of blood from stool, reappearance of formed stool, normalization of weight, body temperature, return of normal appetite and playful activity.

Example 7

Inhibition of PBA Induced CAMP Gene Expression by Cycloheximide

In order to assess whether the PBA and butyrate induction pathways of CAMP gene expression are direct, VA10 cells were treated with PBA or butyrate in the presence and absence of cycloheximide (CHX). After 24 hours of incubation, total RNA was isolated and CAMP mRNA levels measured using real time RT-PCR. Pre-incubating the cells with 20 μg/ml of CHX for one hour prior stimulation effectively blocked both PBA and butyrate induced CAMP gene expression This suggests that that PBA induced CAMP gene expression is induced through a secondary effect. This secondary induction pathway may depend on MAP kinase signaling through JNK and ERK½ as it was shown in VA10, a bronchial epithelial cell line (see FIGS. 6A and 6B).

Example 8

The Effect of PBA on Histone Acetylation at the CAMP Gene Promoter

The effect of PBA on acetylation of histone H3 and H4 by quantitative chromatin immunoprecipitation was assessed. No significant change in histone acetylation could be observed at the CAMP gene proximal promoter (1000 bp upstream of transcription start site) after treatment with 4 mM PBA for 24 hours (FIG. 9)

Earlier it has been assumed that induction of CAMP gene expression by histone deacetylase inhibitors occurs through an increase of histone acetylation and relaxation of chromatin structure, facilitating the binding of other transcription factors. The present data speaks against this hypothesis. Assessing acetylation of H3 and H4 at the CAMP proximal promoter using quantitative chromatin immunoprecipitation, a significant change in acetylation was detectable after treatment with PBA. Furthermore, it was previously shown (see Example 7) that inhibiting protein synthesis using cycloheximide blocks both butyrate and PBA induced expression of CAMP gene expression. These results rule out that an increase of histone acetylation at the CAMP proximal promoter by these compounds directly facilitates CAMP gene expression. Without wishing to be bound by theory, it is believed that an increase of histone acetylation facilitates the expression of other genes, which then increase CAMP gene expression as a secondary effect.

Example 9

The Effect of PBA on Vitamin D Co-Activator Expression

Hypothesizing that the synergistic effect between PBA and $1,25(OH)_2D_3$ was due to an induction of VDR co-activator genes by PBA, we analyzed the effect of PBA on mRNA levels of several known VDR co-activator genes in VA10. None of the genes were significantly upregulated after treatment with 4 mM PBA for 24 hours (see FIG. 10). These co-activators are therefore not involved in the PBA-induced effects on gene expression.

Example 10

Induction of hBD-1 mRNA Expression by PBA

CAMP is not the only antimicrobial defense gene that is induced by PBA. Another well-known peptide is also induced, although at lower level than CAMP (See FIG. 11). This suggests that PBA has a general effect on mucosal defenses.

Example 11

Synthesis of Glyceryl Tributyrate

Butanoic anhydride (164 ml, 1.0 mol) was added during 10 min to glycerol (7.34 ml, 100 mmol) in Pyridine (300 ml) at 0° C. The mixture was stirred at 0° C. for 10 min and at room temperature for 18 h. Water (200 ml) was added and the mixture was heated at 60° C. for 15 min. Evaporation of solvent gave a residue that was partitioned between dichloromethane (DCM, 400 ml) and $NaHCO_3$ (20% in water, 400 ml). The aqueous layer was further extracted with DCM (50 ml). The combined organic extracts were washed first with saturated aqueous $NaHCO_3$ (400 ml) and then with HCl (1 M in water, 400 ml). The organic layer was collected and dried with $Na_2SO_4$ and then concentrated in vacuo to afford 29.6 g (98%) of glyceryl tributyrate $^1$H NMR ($CDCl_3$), 0.95 (t; J=7.4 Hz; 2×$CH_3$), 0.96 (t; J=7.4 Hz; $CH_3$), 1.60-1.73 (m; 3×$CH_2$), 2.31 (t; J=7.4 Hz; 2×$CH_2$), 2.32 (t; J=7.35 Hz; $CH_2$), 4.16 (dd+AB; J=11.9, 6.0 Hz; 2×$CH_a$), 4.31 (dd+AB; J=11.9, 4.3 Hz; 2×$CH_b$), 5.29 (m; 5.26-5.31; CH).

Example 12

Synthesis of N-Butanoylglycine Ethyl Ester

Glycine ethyl ester hydrochloride (13.96 g, 100 mmol) and triethylamine (34.65 ml, 250 mmol) in dichloromethane (DCM, 500 ml) was stirred for 2 h at room temperature, which resulted in a fine white precipitate. Butanoic anhydride (19.63 ml, 120 mmol) in DCM (100 ml) was added over 5 min and the reaction mixture turned to a clear solution. After 30 min at room temperature, and subsequent removal of solvent (in vacuo), water was added (18 ml, 1 mol) followed by pyridine (23.73 g, 24.26 ml, 300 mmol). The solution was heated at 60° C. for 30 min. The mixture was partitioned between DCM (200 ml) and aqueous HCl (2.4 M, 200 ml, saturated with NaCl). The aqueous layer was separated and extracted with DCM (50 ml). The combined organic extract was washed with HCl (aq., 1 M, 250 ml) and the water layer was extracted with an additional portion of DCM (50 ml). The combined organic extracts was washed with $NaHCO_3$ (aq., 4.2%, 200 ml) and the water layer extracted once more with DCM (50 ml). The combined organic extracts was dried with $Na_2SO_4$ and concentrated in vacuo yielding 16.3 g (94%) of N-butanoylglycine ethyl ester. $^1$H NMR ($CDCl_3$), 0.97 (t; J=7.4 Hz; $CH_3$), 1.30 (t; J=7.1 Hz; $CH_3$), 1.65-1.74 (m; $CH_2$), 2.23 (t; J=7.5 Hz; $CH_2$), 4.05 (d; 4.9 Hz; $CH_2$), 4.23 (q; 7.2 Hz; $CH_3$), 5.9 (broad; NH).

Example 13

Synthesis of N-Butanoylglycine

N-Butanoylglycine ethyl ester (16.3 g, 94.16 mmol) was dissolved in aqueous NaOH (1 M, 282 ml, 282 mmol) and then stirred for 15 h at room temperature. Aqueous HCl (12 M, 15.7 ml, 188 mmol) was added to pH=5. The water was then evaporated (in vacuo) and the residue was dissolved in aqueous HCl (1 M, 175 ml) which gave a pH of 1. The solution was saturated with NaCl and extracted with tetrahydrofuran (3×100 ml). The combined organic extracts was dried with $Na_2SO_4$ and evaporated in vacuo yielding 13 g (95%) of N-butanoylglycine. $^1$H NMR ($CDCl_3$), 0.97 (t; J=7.4 Hz; $CH_3$), 1.64-1.74 (m; $CH_2$), 2.27 (t; J=7.5 Hz; $CH_2$), 4.09 (d; J=5.1 Hz; $CH_2$), 6.24 (broad; NH), 8.1 (broad; COOH).

Example 14

Synthesis of $N^{\alpha}$,$N^{\epsilon}$-dibutanoyllysine

Lysine (1 g, 6.1 mmol) was dissolved in 160 ml tetrahydrofuran(THF)-water (1:1), whereupon butanoic anhydride (2.89 g 18.3 mmol) was added. The solution was kept stirring at room temperature and after 1 h 80 ml of THF was added and after standing overnight sodium carbonate decahydrate was added (5.23 g, 18.3 mmol). After this mixture was stirred for ca 30 min another portion of butanoic anhydride (2.89 g 18.3 mmol) was added and the mixture was again kept stirring overnight. The mixture was saturated with sodium chloride and made acidic with concentrated HCl (to about pH 1). The top layer was separated and the solvent was evaporated. To the residue 400 ml 0.125 M NaOH (aq) and 100 ml THF was added. After ca 15 the THF was evaporated and the solution was washed with chloroform (2×200 ml). The aqueous phase was then acidified with 7 ml conc. HCl (aq) and extracted with chloroform-methanol (4:1, 2×250 ml). The organic phase was dried with sodium sulfate, filtered and concentrated under reduced pressure. The remaining butanoic acid was removed by repeated evaporation of added formic acid-water (3:1) under reduced pressure to give 1.32 g (79%) of product. $^1$H NMR ($CDCl_3$), 0.92-0.98 (m, 6H; $2\times CH_3$), 1.3-1.48 (m, 2H; $CH_2$), 1.54 (qv, 2H, J=6.8 Hz; $CH_2$), 1.62-1.70 (m, 4H; $2\times CH_2$), 1.75-1.83 (m, 2H; $CH_2$), 1.85-1.95 (m, 2H; $CH_2$), 2.18 (t, 2H, J=7.3 Hz; $CH_2$), 2.25 (t, 2H, J=6.2 Hz; $CH_2$), 3.17-3.22 (m, 1H; $\epsilon$-$CH_{2a}$), 3.31-3.37 (m, 1H; $\epsilon$-$_{CH2b}$), 4.52-4.58 (m, 1H; $\alpha$CH), 6.08 (bs, 1H; $\epsilon$-NH), 6.86 (d, 1H, J=7.3 Hz; $\alpha$-NH).

Example 15

Demonstration of Effectiveness of Butyrate-Class Compounds in Human Infectious Colitis (Shigellosis)

The following trial is performed with sodium butyrate enema but may be performed correspondingly using PBA for oral administration.

Requirement of a Population

Sodium butyrate enemas have been applied in inflammatory bowel diseases, including ulcerative colitis, diversion colitis, Crohn's Diseases but never in an infectious colitis.

Adult patients with shigellosis have been selected to assess the efficacy in infectious colitis which may be later conducted in children.

Selection of Butyrate Enema Over Oral Tablets

A large body of evidence is available to show that sodium butyrate enema given over a range of 2-6 weeks in adult patients with inflammatory bowel disease (IBD) is safe with no obvious side effects. The topical dosage used in various previous studies ranged from 528 mg/day to 1.12 g/day, which corresponds to 35-60% of the normal daily intracolonic production of butyrate. None of these studies reported any adverse effect or reactions. According to one study, daily oral dose of 4 g of sodium butyrate given as colonic-targeted tablets for 6-weeks in IBD patients and was also found safe and well tolerated without any adverse effects. The present study utilised enema.

Study design: A double blind randomized clinical trial with subsequent follow-up.

Study Subjects: Adult male and female patients attending the Dhaka Hospital and Matlab Hospital of ICDDR, B are screened for participation in the study.

Inclusion Criteria:

18-45 years of age

Males & females duration of diarrhoea 0-3 days culture-confirmed *Shigella* spp (all *Shigella* spp) in stool on enrolment Exclusion Criteria:

who received antimicrobial treatment before attending the ICDDR, B hospital clinical symptoms of other concomitant infections (such as chronic respiratory infections, other concomitant gastrointestinal infections)

Randomization

According to a computer-generated randomization list, patients full filling the entry criteria is randomized to either intervention group (Pivmecillinam plus butyrate enema) or control/placebo group (Pivmecillinam plus normal saline enema).

Composition of Enema and Procedure for Enema

Butyrate enema contains 80 mmol/L of butyrate in normal saline (pH 7.2).

Placebo enema contains 30 mmol/L NaCl (pH 7.2).

The patient is instructed to lie on a bed (cholera cot) in left lateral position. A soft rectal catheter is introduced by a nurse/physician, through which 80 ml of butyrate solution is instilled slowly with a 50 ml plastic syringe. The patient is asked to retain the enema for at least ½ hour by remaining supine for 30 minutes after the administration. However, if a patient cannot retain the enema for 30 minutes, he is given a second round of enema immediately after defecation.

Case Management

After enrolment, the patients are admitted in the study ward of ICDDRB Dhaka and Matlab hospital. A standard clinical history and clinical examination is performed by the study physician. All patients receive Pivmecillinam, 400 mg, 8 hourly for 5 days. The intervention group receives butyrate enema 80 ml of 80 mM sodium butyrate, 12 hourly for 72 hours while the placebo group gets 80 ml of normal saline 12 hourly for 72 hours. All patients receive the usual hospital food three times a day (breakfast, lunch and supper). The patients remain in the study ward for 5 days to enable identification of any relapse cases.

Sample Size

In a study by Kabir I et al (1984) (Kabir I, Rahaman M M, Ahmed S M, Akhter S Q, Butler T. *Comparative efficacies of pivmecillinam and ampicillin in acute shigellosis. Antimicrob Agents Chemother.* 1984 May; 25(5):643-5.), it has been shown with 3.2±1.8 (mean±SD) duration of diarrhoea of patients with shigellosis while treated with pivmecillinam. Expecting a 30% reduction in duration of diarrhoea when treated with butyrate enema along with pivmecillinam, considering 5% level of significance and 80% power the sample size will be 55 per group. Considering a dropout of 10%, the sample size in each group will be 61.

Clinical Parameters Measured/Recorded

1. Appetite
2. Abdominal cramps
3. Rectal tenesmus
4. Body temperature, 8 hourly
5. Daily frequency of stool (No. of times of defecation)
6. Stool output (in grams)
7. Presence of RBC, pus cells and macrophages in stool by RME
8. Weight at admission, daily during hospitalization and after 14 days (at follow-up)
9. Sigmoidoscopic findings Other Analysis 1. Stool culture by serial dilution method for bacterial count (twice daily) for 4 days.
2. Stool for detection of LL-37 by Western blot 3. Stool for determination of LL-37 by ELISA
4. Rectal biopsy (from Dhaka patients only) for histologic grading of inflammation.
5. Rectal biopsy for immunohistochemical staining of LL-37 and image analysis.
6. Rectal biopsy for assessing transcripts of LL-37 in tissue by realtime PCR.
7. Serum for measuring butyrate Data Analysis For normally distributed data, it is intended to use appropriate parametric tests (eg. t test) to compare the results between groups. In case the data is skewed, nonparametric tests will be used. Statistical analysis can then be done using two-factor ANOVA to determine significant interactions between time and treatment and in case of any significant interactions post hoc Tukey procedure will be performed. For data that are not normally distributed, ANOVA on ranks will be applied. For within group (between days) comparisons, one-way ANOVA will be done. Statistical calculations will be performed using the statistical software SigmaStat® 3.1 (Jandel Scientific, San Rafael, Calif.) and SPSS13.

The invention claimed is:

1. A method of treating a microbial infection in an animal by stimulating the innate antimicrobial peptide defense system, the method comprising administering to the animal a medicament comprising a compound, wherein the compound is 4-phenylbutyric acid and wherein the infection is a bacterial infection caused by a microbial species selected from the group consisting of *Shigella* and *E. Coli.*

2. The method of claim 1, wherein the medicament comprises the compound in an amount of 1 g to 10 g daily.

3. The method of claim 1, wherein the medicament is a pharmaceutical composition comprising a unit dose of the compound in the range of about 10-1000 mg and at least one pharmaceutically acceptable excipient, wherein the dose is administered daily.

4. The method of claim 1, wherein the medicament is administered in the treatment at less than 720 mg daily.

5. The method of claim 1, wherein the infection is a bacterial infection caused by *Shigella.*

6. The method of claim 1, wherein the infection results in a gastrointestinal disorder selected from the list consisting of traveller's diarrhoea, and endemic diarrhoea.

7. The method of claim 1, wherein the infection is an infection of the respiratory system.

8. The method of claim 1, wherein the method is a combination method for treating the microbial infection in the animal, wherein the compound is used in combination with any one or more of: an antibiotic; an aminosterol-type compound; isoleucine or active isomers or analogs thereof; or a vitamin D type compound.

9. The method of claim 8, wherein the compound is used in combination with vitamin D.

10. The method of claim 1, wherein the medicament is in an oral dosage form.

11. The method of claim 1, wherein the animal is a human.

12. The method of claim 1, wherein the medicament is administered orally.

* * * * *

SEQUENCE LISTING

```
<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: Synthetic

<400> SEQUENCE: 1

tgttatcctt atcacaactg at                                              22


<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2

acccagcagg gcaaatctc                                                  19


<210> SEQ ID NO 3
<211> LENGTH: 19
<212> TYPE: DNA
<213> ORGANISM: Artificial Sequence
<220> FEATURE:
<223> OTHER INFORMATION: Synthetic

<400> SEQUENCE: 3

gaaggacggg ctggtgaag                                                  19
```